(12) United States Patent
Urano et al.

(10) Patent No.: US 10,203,601 B2
(45) Date of Patent: Feb. 12, 2019

(54) TETRACARBOXYLIC ACID DIESTER COMPOUND, POLYMER OF POLYIMIDE PRECURSOR AND METHOD FOR PRODUCING SAME, NEGATIVE PHOTOSENSITIVE RESIN COMPOSITION, PATTERNING PROCESS, AND METHOD FOR FORMING CURED FILM

(71) Applicant: SHIN-ETSU CHEMICAL CO., LTD., Tokyo (JP)

(72) Inventors: Hiroyuki Urano, Jyoetsu (JP); Katsuya Takemura, Jyoetsu (JP); Masashi Iio, Jyoetsu (JP); Koji Hasegawa, Jyoetsu (JP); Kenji Funatsu, Jyoetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 15/705,842

(22) Filed: Sep. 15, 2017

(65) Prior Publication Data

US 2018/0120702 A1    May 3, 2018

(30) Foreign Application Priority Data

Oct. 27, 2016 (JP) .................. 2016-210865

(51) Int. Cl.
| | | |
|---|---|---|
| *C07F 7/08* | (2006.01) | |
| *C07F 7/18* | (2006.01) | |
| *G03F 7/16* | (2006.01) | |
| *G03F 7/20* | (2006.01) | |
| *G03F 7/32* | (2006.01) | |
| *G03F 7/38* | (2006.01) | |

(Continued)

(52) U.S. Cl.
CPC ............ *G03F 7/0387* (2013.01); *C07C 69/76* (2013.01); *C07F 7/081* (2013.01); *C07F 7/0838* (2013.01); *C07F 7/1804* (2013.01); *C07F 7/1892* (2013.01); *C08G 73/105* (2013.01); *C08G 73/106* (2013.01); *C08G 73/1046* (2013.01); *C08G 73/1053* (2013.01); *C08G 73/1071* (2013.01); *C08G 73/121* (2013.01); *C08G 77/045* (2013.01); *G03F 7/0045* (2013.01); *G03F 7/037* (2013.01); *G03F 7/0757* (2013.01); *G03F 7/0758* (2013.01); *G03F 7/162* (2013.01); *G03F 7/168* (2013.01); *G03F 7/2004* (2013.01); *G03F 7/325* (2013.01); *G03F 7/38* (2013.01); *G03F 7/40* (2013.01)

(58) Field of Classification Search
CPC ...... C07C 69/76; C07F 7/0818; C07F 7/0852; G07F 7/0758; C08G 73/1046; C08G 73/121; C08G 73/105; C08G 73/106; C08G 77/045

USPC .............................. 430/283.1, 287.1
See application file for complete search history.

(56) References Cited

U.S. PATENT DOCUMENTS

| | | | |
|---|---|---|---|
| 3,957,512 A | 5/1976 | Kleeberg et al. | |
| 5,114,826 A * | 5/1992 | Kwong ............... | G03F 7/0387 |
| | | | 252/600 |

(Continued)

FOREIGN PATENT DOCUMENTS

| | | | | |
|---|---|---|---|---|
| EP | 0554040 A2 * | 8/1992 | | |
| EP | 0512692 A1 * | 11/1992 | ........... | C08G 73/106 |

(Continued)

OTHER PUBLICATIONS

Chin et al, "Synthesis and characterization of various esters of the oxydianiline/pyromellitic dianhydride polyamic acid " in Polyimides Other High-Temp. Polym., Proc. Eur. Tech. Symp., 2$^{nd}$ / Polyimides Other High-Temp. Polym., Proc. Eur. Tech. Symp., 2$^{nd}$, pp. 19-33, Year publication 1991.*

(Continued)

*Primary Examiner* — Cynthia Hamilton
(74) *Attorney, Agent, or Firm* — Oliff PLC

(57) ABSTRACT

The present invention provides a tetracarboxylic acid diester compound represented by the following general formula (1),

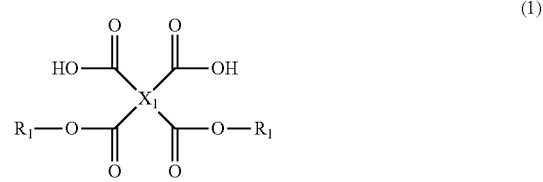

(1)

wherein, $X_1$ represents a tetravalent organic group, and $R_1$ represents a group represented by the following general formula (2),

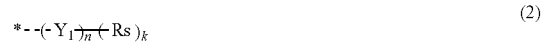

(2)

wherein, the dotted line represents a bonding, $Y_1$ represents an organic group with a valency of k+1, Rs represents a group containing at least one silicon atom, "k" represents 1, 2 or 3, and "n" represents 0 or 1. There can be provided a tetracarboxylic acid diester compound which can lead a polymer of a polyimide precursor capable of using a base resin of a negative photosensitive resin composition which is capable of forming a fine pattern and giving high resolution, a polymer of a polyimide precursor obtained by using the tetracarboxylic acid diester compound and a method for producing the same.

2 Claims, No Drawings

(51) Int. Cl.
*G03F 7/40* (2006.01)
*C07C 69/76* (2006.01)
*C08G 73/10* (2006.01)
*C08G 73/12* (2006.01)
*C08G 77/04* (2006.01)
*G03F 7/004* (2006.01)
*G03F 7/037* (2006.01)
*G03F 7/038* (2006.01)
*G03F 7/075* (2006.01)

(56) References Cited

U.S. PATENT DOCUMENTS

| | | | |
|---|---|---|---|
| 6,001,534 A | 12/1999 | Kato | |
| 6,071,666 A | 6/2000 | Hirano et al. | |
| 6,235,436 B1 | 5/2001 | Hirano et al. | |
| 7,851,121 B2* | 12/2010 | Yamanaka | G03F 7/0046 430/191 |
| 2012/0088888 A1 | 4/2012 | Nagao | |
| 2012/0202117 A1* | 8/2012 | Hirose | H01M 4/134 429/211 |
| 2015/0307662 A1* | 10/2015 | Oka | C08G 73/10 528/125 |

FOREIGN PATENT DOCUMENTS

| | | |
|---|---|---|
| EP | 0 807 852 A1 | 11/1997 |
| JP | 49-115541 A | 11/1974 |
| JP | 55-45746 A | 3/1980 |
| JP | 3232022 B2 | 11/2001 |
| JP | 2005-049504 A | 2/2005 |
| JP | 3627488 B2 | 3/2005 |
| JP | 5417623 B2 | 2/2014 |
| KR | 10-533488 B1 | 4/2006 |
| KR | 10-2014-0148451 A | 12/2014 |
| WO | 2013/168675 A1 | 11/2013 |

OTHER PUBLICATIONS

Kim et al "Synthesis and Characterization of New Organosoluble and Gas-Permeable Polyimides from Bulky Substituted Pyromellitic Dianhydrides" Journal of Polymer Science: Part A: Polymer Chemistry, vol. 40, 4288-4296 (2002) (Year: 2002).*

Abadie ed.TItle: Polyimides and other High-Temperature Polymers, Proceedings of the 2nd European Technical Symposium on POlyimides and High-Temperature Polymers (Stepi 2),: Montpellier, France Jun. 4-7, 1991, Elsevier ,Amsterdam 1991, Article of Chin et al , pp. 19-33. (Year: 1991).*

Chin et al., "Synthesis and characterization of various esters of the oxydianiline/pyromellitic dianhydride polyamic acid," retrieved from STN Database Accession No. XP002776729, 1993.

Feb. 5, 2018 extended European Search Report issued in Application No. 17001603.4.

Nov. 20, 2018 Office Action Issued in Korean Patent Application No. 2017-0141361.

* cited by examiner

TETRACARBOXYLIC ACID DIESTER COMPOUND, POLYMER OF POLYIMIDE PRECURSOR AND METHOD FOR PRODUCING SAME, NEGATIVE PHOTOSENSITIVE RESIN COMPOSITION, PATTERNING PROCESS, AND METHOD FOR FORMING CURED FILM

TECHNICAL FIELD

The present invention relates to a tetracarboxylic acid diester compound useful as a structural unit of a polyimide precursor, a polymer of a polyimide precursor obtained by using the tetracarboxylic acid diester compound and a method for producing the same, a negative photosensitive resin composition using the polymer of a polyimide precursor as a base resin, a patterning process using the negative photosensitive resin composition, and a method for forming a cured film.

BACKGROUND ART

As various electronic devices such as a personal computer, a digital camera, a mobile phone, etc., progress toward miniaturization and high performances, demands for further miniaturization, thinning and high density are rapidly required in a semiconductor device. Therefore, it has been desired to develop a photosensitive insulating material which can cope with increase in a substrate area for improvement in productivity, and, can form a fine film with high aspect ratio on a substrate in the high density mounting technology such as a chip size package, a chip scale package (CSP) and three-dimensional lamination.

In the high density mounting technology like a three-dimensional lamination, as a photosensitive insulating material which is able to subjecting to patterning on the substrate, a polyimide film has been used as a protective film or an insulating layer, and its insulating property, mechanical strength, adhesiveness to the substrate, etc., are continuously attracted attention, and development thereof is vigorous even now.

As a photosensitive polyimide-based material, a material utilizing a polyamic acid which is a precursor of polyimide, for example, a material in which a photosensitive group is introduced into a carboxyl group of the polyamic acid by an ester bond (Patent document 1, Patent document 2) has conventionally been proposed. However, in these proposals, imidation treatment at a high temperature exceeding 300° C. is indispensable in order to obtain a target polyimide film after formation of a patterned film, so that it involved the problems that an underlying substrate is restricted to endure this high temperature and the copper of the wiring is oxidized.

As an improvement thereof, it has been proposed a photosensitive polyimide using an already imidated solvent-soluble resin for the purpose of lowering the post-curing temperature (Patent document 3, Patent document 4). In a negative photosensitive resin composition using a polyimide described in Patent document 3, development using N-methyl-2-pyrrolidone (NMP) is carried out in patterning, but there is not described in Patent document 3 about specific description on resolution in the patterning.

On the other hand, the photosensitive resin composition proposed in Patent document 4 uses an already imidated base resin which has been constructed in view of low temperature curing. The solvent of the composition is cyclopentanone, and an alkaline aqueous solution is used in developing. However, improvement in resolution has yet been required. That is, patterning using a photosensitive resin composition described in Patent document 4 has been carried out with an extremely thin film, and a pattern size to be resolved is large. This lack of resolution performance is due to poor solubility of the polyimide resin, which is the base resin disclosed in Patent Document 4, in an alkaline aqueous solution used for a developer. It is a key for improving the resolution performance in patterning to heighten solubility of a resin in a developer.

In fact, as the resolution performance of the photosensitive insulating material in the high density mounting technology such as the three-dimensional lamination which is required in recent years, the aspect ratio (film thickness at the time of finishing (or height of pattern)/pattern dimension) of the formed pattern is required to be 1 or more and 2 or so. That is, when the desired film thickness at the time of finishing or the height of the pattern is 10 μm, a pattern with a dimension of 10 μm or less or a dimension of near 5 μm must be formed.

By the way, in Patent document 5, there is an example of a patterning process of a photosensitive resin composition using a material utilizing a polyamic acid which is a precursor of a polyimide, for example, a resin in which an ester bond is introduced into the carboxyl group of the polyamic acid, where, after forming a film, heating to be applied to obtain an objective polyimide film is carried out at a relatively low temperature of 250° C. While an organic solvent of N-methyl-2-pyrrolidone is used in the development, there is no disclosure about specific resolution in this Patent document.

With regard to patterning of the negative photosensitive resin composition using a precursor of a polyimide, there is Patent document 6. In the development of the patterning of the photosensitive resin composition, cyclopentanone is used. With regard to resolution performance, it has been specifically disclosed, and disclosed that an aspect ratio of 1 or more can be accomplished. However, this aspect ratio does not represent a ratio of a film thickness at the time of finishing or a height of the pattern to a dimension of the pattern, but a ratio of a film thickness after coating and drying to a dimension, so that this resolution performance is not a practical value, and an improvement is required. It is preferred to use a versatile organic solvent such as cyclopentanone as a developer, but when an organic solvent is used, the defect that a pattern profile immediately after the development likely becomes an overhang profile sometimes occurs due to swelling of the film during the development.

Further, with regard to patterning of the negative photosensitive resin composition using a precursor of a polyimide, there is Patent document 7. The developer in the patterning of the photosensitive resin composition is an alkaline aqueous solution. In this patterning process, solubility to the alkaline aqueous solution of the developer is improved by introducing an acid group into the resin of the polyimide precursor, i.e., an alkali-soluble group such as a carboxyl group, patterning by the development using the alkaline aqueous solution is carried out. The development using the alkaline aqueous solution has advantages that it difficulty causes swelling, a pattern profile becomes good and resolution performance is also improved. However, when an alkali-soluble group which enables the development using the alkaline aqueous solution is introduced into the resin, whereas it works dominantly in improving the resolution, it cannot avoid the problem that resistance to an extremely strong alkaline peeling liquid used for peeling the resist pattern for plating used in metal wiring process after curing is impaired. In order to form an excellent protective insulating film, it is necessary to completely seal the alkali-soluble groups present onto the resin or completely remove them from the system.

Thus, accompanied by high densification and high integration of the chips, miniaturization of the pattern in the rewiring technology of the insulating protective film is expected to be promoted more and more in the future, so that in the photosensitive resin composition using a polymer having a polyimide precursor structural unit, a composition which can realize high resolution without impairing excellent characteristics of a pattern of the polyimide obtained by heating and mechanical strength, adhesiveness, etc., of the protective film has been strongly desired.

It has been also strongly desired that the insulating protective film subjected to patterning and curing has heat resistance in various processes and resistance to various chemicals to be used.

That is, rapid development of the photosensitive resin composition having all of these features without lacking any of these has been desired.

CITATION LIST

Patent Literature

Patent Document 1: Japanese Unexamined Patent Application Publication No. S49-115541
Patent Document 2: Japanese Unexamined Patent Application Publication No. S55-45746
Patent Document 3: Japanese Patent No. 3232022
Patent Document 4: Japanese Patent No. 5417623
Patent Document 5: Japanese Unexamined Patent Application Publication No. 2005-49504
Patent Document 6: WO2013/168675
Patent Document 7: Japanese Patent No. 3627488

SUMMARY OF INVENTION

Technical Problem

The present invention has been done in view of the circumstance, and an object thereof is to provide a tetracarboxylic acid diester compound which can be led to a polymer of a polyimide precursor that can be used as a base resin of a negative photosensitive resin composition which can form a fine pattern and can obtain high resolution, a polymer of a polyimide precursor obtained by using the tetracarboxylic acid diester compound and a method for producing the same.

In addition, the other objects are to provide a negative photosensitive resin composition using a polymer of a polyimide precursor as a base resin which can accomplish improvement in resolution due to large difference in dissolution rates between an unexposed portion (a portion dissolving in the developer) and an exposed portion (the portion which becomes insoluble in the developer by the crosslinking reaction, photopolymerization, etc.) of the negative pattern obtained by high solubility in the developer of an organic solvent in the patterning, i.e., high contrast in dissolution, without impairing the pattern profile by generating swelling, etc., when the development by an organic solvent is carried out, and to provide a negative photosensitive resin composition which can make an organic solvent when the development by an organic solvent is carried out a versatile and safety organic solvent.

Solution to Problem

To solve the problems, according to the present invention, it is provided a tetracarboxylic acid diester compound represented by the following general formula (1),

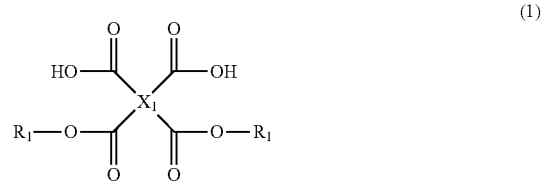

wherein, $X_1$ represents a tetravalent organic group, and $R_1$ represents a group represented by the following general formula (2),

wherein, the dotted line represents a bonding, $Y_1$ represents an organic group with a valency of k+1, Rs represents a group containing at least one silicon atom, "k" represents 1, 2 or 3, and "n" represents 0 or 1.

When such a tetracarboxylic acid diester compound is employed, it can obtain a polymer of a polyimide precursor useful as a base resin of a negative photosensitive resin composition which can heighten solubility in development by an organic solvent in a patterning and can avoid swelling.

At this time, $Y_1$ in the general formula (2) is preferably a linear or branched divalent organic group having 1 to 6 carbon atoms.

When such a material is used, the effects of the present invention can be sufficiently obtained.

Also, at this time, $R_1$ in the general formula (1) is preferably a group represented by the following general formula (3) or the following general formula (4),

wherein, the dotted line represents a bonding, Rs represents the same meaning as before, Ra and Rb each independently represent a hydrogen atom or an alkyl group having 1 to 3 carbon atoms, $Y_2$ represents a linear or branched alkylene group having 1 to 6 carbon atoms, "n1" represents an integer of 1 to 6, "n2" represents an integer of 1 to 6 and "n3" represents an integer of 1 to 6.

Moreover, $R_1$ in the general formula (1) is preferably a group represented by the following general formula (5),

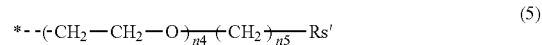

wherein, the dotted line represents a bonding, "n4" represents an integer of 1 to 6, "n5" represents an integer of 1 to 6, and Rs' is a group represented by the following general formula (6),

(6)

wherein, Rc to Rg each may be the same or different from each other and represent a monovalent hydrocarbon group having 1 to 8 carbon atoms, and "l" represents an integer of 1 to 100.

When $R_1$ in the general formula (1) is such a group, solubility in an organic solvent as the developer can be sufficiently heightened.

Also, in the present invention, it is provided a polymer of a polyimide precursor containing a structural unit represented by the following general formula (7),

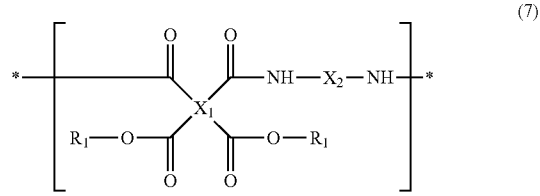

(7)

wherein, $X_1$ represents a tetravalent organic group, $X_2$ represents a divalent organic group, $R_1$ represents a group represented by the following general formula (2),

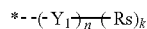

(2)

wherein, the dotted line represents a bonding, $Y_1$ represents an organic group with a valency of k+1, Rs represents a group containing at least one silicon atom, "k" represents 1, 2 or 3, and "n" represents 0 or 1.

Here, the polymer of a polyimide precursor having the structural unit represented by the general formula (7) can be led from the tetracarboxylic acid diester compound represented by the general formula (1), and the tetracarboxylic acid diester compound represented by the general formula (1) has a group $R_1$ represented by the general formula (2) (for example, an organic group selected from the groups represented by the formulae (3) and (4)) and the $R_1$ has Rs, which contains at least one silicon atom, at the terminal of the substituent. In general, many of the polymers having a structural unit of a polyimide precursor have characteristics that these dissolve only in a polar solvent such as N-methyl-2-pyrrolidone. The Rs group (in particular, a siloxane unit represented by the formula (6)), which contains at least one silicon atom, is introduced at the terminal of a substituent as in the structural unit of the polyimide precursor represented by the general formula (7) derived from the tetracarboxylic acid diester compound represented by the general formula (1) to have the Rs group to the polymer molecule, it is possible to constitute a negative photosensitive resin composition which is easily soluble in a versatile organic solvent, solubility in the versatile organic solvent to be used for the development by an organic solvent is further increased and resolution is improved.

In addition, the polymer of a polyimide precursor having the structural unit represented by the general formula (7) contains the group $R_1$ represented by the general formula (2) (for example, an organic group selected from the groups represented by the formulae (3) and (4)), and the $R_1$ contains the Rs group, which contains at least one silicon atom, at the terminal of a substituent, so that in the case where a film formed by the polymer or a film formed by using a composition containing the polymer is to be dissolved in an organic solvent, it has characteristics that it difficulty causes swelling.

At this time, it is preferred that the polymer of a polyimide precursor further contains a structural unit represented by the following general formula (8),

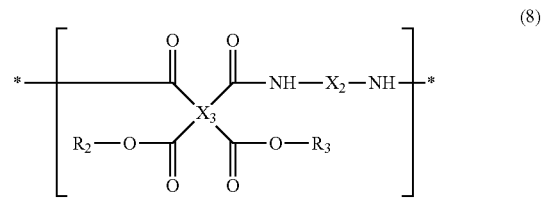

(8)

wherein, $X_2$ represents the same meaning as before, $X_3$ represents a tetravalent organic group which is the same as or different from that of the $X_1$; $R_2$ and $R_3$ each independently represent a hydrogen atom, a linear, branched or cyclic alkyl group having 1 to 6 carbon atoms, or an organic group represented by the following general formula (9), and at least one of $R_2$ and $R_3$ is an organic group represented by the following general formula (9),

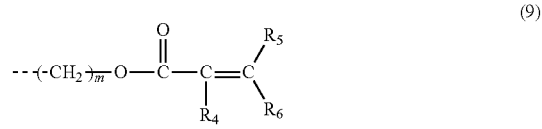

(9)

wherein, the dotted line represents a bonding, $R_4$ represents a hydrogen atom or an organic group having 1 to 3 carbon atoms, $R_5$ and $R_6$ each independently represents a hydrogen atom or an organic group having 1 to 3 carbon atoms, and "m" represents an integer of 2 to 10.

When such a material is employed, it has a polymerizable unsaturated bonding group in the structural unit, so that by using it with the photoradical initiator mentioned later in combination, radical polymerization proceeds in the patterning using radicals generating at the exposed portion as an initiator, whereby it has a characteristic that it becomes insoluble in the developer, and the negative photosensitive resin composition can be provided without newly adding a crosslinking agent.

In the present invention, it is also provided a method for producing the polymer of a polyimide precursor containing the structural unit represented by the general formula (7), which comprises reacting a tetracarboxylic acid diester compound represented by the following general formula (1) and a diamine represented by the following general formula (10),

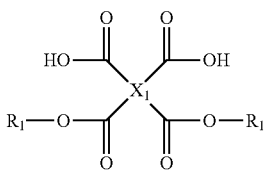

(1)

wherein, $X_1$ and $R_1$ represent the same meanings as before, $$H_2N-X_2-NH_2 \quad (10)$$

wherein, $X_2$ represents the same meaning as before.

The polymer of a polyimide precursor containing the structural unit represented by the general formula (7) can be produced, for example, by such a method.

Moreover, in the present invention, it is provided a method for producing the polymer of a polyimide precursor containing the structural unit represented by the general formula (8), which comprises reacting a tetracarboxylic acid diester compound represented by the following general formula (1), a diamine represented by the following general formula (10) and a tetracarboxylic acid diester compound represented by the following general formula (11),

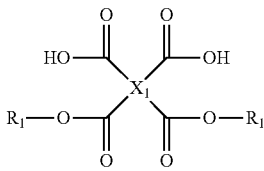

(1)

wherein, $X_1$ and $R_1$ represent the same meanings as before, $$H_2N-X_2-NH_2 \quad (10)$$

wherein, $X_2$ represents the same meaning as before,

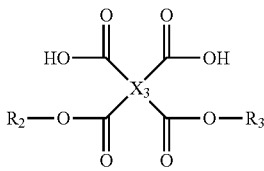

(11)

wherein, $X_3$, $R_2$ and $R_3$ represent the same meanings as before.

The polymer of a polyimide precursor containing the structural unit represented by the general formula (8) can be produced, for example, by such a method.

Furthermore, in the present invention, it is provided a negative photosensitive resin composition which comprises
(A) a polymer of a polyimide precursor containing the structural unit represented by the general formula (8),
(B) a photo-radical initiator, and
(D) a solvent.

As stated above, the polymer of a polyimide precursor containing the structural unit represented by the general formula (8) has a polymerizable unsaturated bonding group in the polymer molecules, so that by the combination of the polymer and the photoradical initiator, a negative photosensitive resin composition can be obtained.

Also, in the present invention, it is provided a negative photosensitive resin composition which comprises
(A') the polymer of a polyimide precursor,
(B) a photo-radical initiator,
(C) a crosslinking agent having two or more photo-polymerizable unsaturated bonding group in one molecule, and
(D) a solvent.

Here, the polymer of a polyimide precursor containing no structural unit represented by the general formula (8) is estimated to be the case where it does not have a structure which can be polymerizable or crosslinkable in the polymer molecules. Therefore, by complementing a crosslinking agent having a photo-polymerizable unsaturated bonding group, it is possible to constitute a negative type composition. On the other hand, whereas the polymer of a polyimide precursor containing the structural unit represented by the general formula (8) already has a polymerizable unsaturated bonding group in the molecule of the polymer, it is also possible to newly add a crosslinking agent.

Further, in the present invention, it is provided a negative photosensitive resin composition which comprises
(A') the polymer of a polyimide precursor,
(B') a photo-acid generator,
(C') one kind or two or more kinds of a crosslinking agent(s) selected from the group consisting of an amino condensate modified by formaldehyde or formaldehyde-alcohol, a phenol compound having two or more methylol groups or alkoxymethylol groups in an average in one molecule, a compound in which a hydrogen atom of a hydroxyl group of a polyvalent phenol is substituted by a glycidyl group, a compound in which a hydrogen atom of a hydroxyl group of a polyvalent phenol is substituted by a substituent represented by the following formula (C-1), and a compound containing two or more nitrogen atoms each of which has a glycidyl group(s) represented by the following formula (C-2a) or the following formula (C-2b),

(C-1)

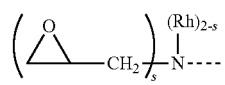

(C-2a)

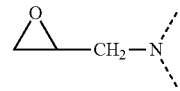

(C-2b)

wherein, the dotted line represents a bonding, $R_h$ represents a linear, branched or cyclic alkyl group having 1 to 6 carbon atoms, and "s" represents 1 or 2, and (D) a solvent.

Thus, by using the photoacid generator of Component (B'), in the patterning, an acid is generated at the exposed portion to crosslink the crosslinking group of the crosslinking agent of the added Component (C') and the reaction sites of the polymer, whereby it can be made a composition which can give a negative image by becoming insoluble in the developer.

Moreover, in the present invention, it is provided a patterning process which comprises
(1) coating the negative photosensitive resin composition onto a substrate to form a film of a photosensitive material, then,
(2) after heat treatment, exposing the film of a photosensitive material by a high energy beam having a wavelength of 190 to 500 nm or an electron beam through a photomask, and
(3) developing the film by using a developer of an organic solvent.

The polymer of a polyimide precursor of the base resin of the negative photosensitive resin composition of the present invention contains the structural unit represented by the general formula (7), so that it contains an Rs group, which contains at least one silicon atom, at the terminal of the substituent, and due to the presence of the Rs group, solubility of the developer in an organic solvent is increased, whereby the effect of suppressing worried swelling can be obtained. In addition, such a patterning process is, in particular, suitable for a negative photosensitive resin composition using the polymer having a polymerizable unsaturated bonding group as a base resin.

At this time, it is preferred to contain a post-exposure bake step between the exposing step and the developing step.

In particular, in the case of the negative photosensitive resin composition containing the polymer of a polyimide precursor containing the structural unit represented by the general formula (8), by containing the heating (post exposure bake (PEB)) after exposing, the crosslinking reaction at the crosslinking group of the crosslinking agent and the crosslinking reaction site of the polymer can be promoted using an acid generated from the photoacid generator by exposure as a catalyst.

Furthermore, in the present invention, it is provided a method for forming a cured film which comprises heating and post-curing a pattern-formed film obtained by the patterning process at a temperature of 100 to 300° C.

The polymer of a polyimide precursor of the present invention has an Rs group containing at least one silicon atom at the terminal of the substituent, in the post-curing, an imide ring-closing reaction is generated at the structural unit of the polyimide precursor in the polymer of a polyimide precursor and the Rs group is eliminated, but when the Rs particularly has a siloxane unit represented by the general formula (6), etc., it remains in the cured film. According to this, electric characteristics such as a dielectric constant, etc., which is important as an insulating material, are improved, and the film becomes an extremely stable polyimide resin completely ring closed. Thus, a cured film extremely improved in chemical resistance, in particular, resistance to a peeling liquid with an extremely strong alkaline to be used for peeling a resist pattern for plating used for applying metal wiring can be formed. These cured films having a pattern can be made a protective film for electric and electronic parts, or an insulating protective film.

Advantageous Effects of Invention

According to the present invention, it is possible to provide a tetracarboxylic acid diester compound capable of giving a polymer of a polyimide precursor which can be used as a base resin of an organic solvent development type negative photosensitive resin composition. In patterning using the negative photosensitive resin composition containing the polymer of a polyimide precursor obtained from such a tetracarboxylic acid diester compound, development using a versatile and safety organic solvent becomes possible, and solubility in the developer becomes sufficiently high, so that the resolution can be improved. Further, swelling hardly occurs in development, so that a fine pattern having a good pattern profile can be obtained.

Furthermore, according to the present invention, by subjecting to post-curing of the obtained pattern-formed film, a protective film excellent in chemical resistance can be provided since a substituent having high solubility in the organic solvent, which had worked dominantly for improving resolution in the patterning, is eliminated by the imide ring-closing reaction to give a stable polyimide film. In addition, the resulting film becomes a protective film excellent in mechanical strength, adhesiveness to the substrate, electric characteristics and reliability which are characteristics of polyimide.

DESCRIPTION OF EMBODIMENTS

As mentioned above, it is desired to develop a tetracarboxylic acid diester compound capable of providing a polyimide precursor polymer usable as a base resin of a negative photosensitive resin composition that allows the development with a widely used safe organic solvent, sufficiently increases the solubility in this developer, and thus can improve the resolution, enabling a fine pattern to be formed.

The present inventors have intensively studied to accomplish the objects, and as a result, they have found that a polymer (the polymer of a polyimide precursor) having a structural unit of a polyimide precursor obtained by using the tetracarboxylic acid diester compound represented by the following general formula (1) is used as a base resin, the polymer is easily soluble in a versatile and safety organic solvent so that it is useful for constituting a composition, and the polymer can be applied to a negative photosensitive resin composition capable of subjecting to development by an organic solvent, whereby the pattern obtained by using the negative photosensitive resin composition is fine and has a good pattern profile. In addition, the polymer having a structural unit of a polyimide precursor obtained by using the tetracarboxylic acid diester compound represented by the following general formula (1) is easily soluble in a versatile and safety organic solvent, so that when development by an organic solvent is carried out, they have found an advantage that a versatile and safety organic solvent can be used.

Moreover, they have found that a protective film obtained by using the negative photosensitive resin composition using a polymer having a structural unit of a polyimide precursor as a base resin, and subjected to patterning and heating is excellent in mechanical strength and adhesiveness. That is, the cured film having a pattern formed by using the negative photosensitive resin composition which contains a polymer having a structural unit of a polyimide precursor as a base resin is excellent as a protective film for electric and electronic parts and an insulating protective film, whereby they have accomplished the present invention.

That is, the present invention is a tetracarboxylic acid diester compound represented by the following general formula (1),

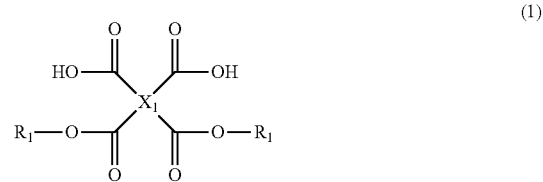

(1)

wherein, $X_1$ represents a tetravalent organic group, and $R_1$ represents a group represented by the following general formula (2),

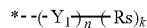
(2)

wherein, the dotted line represents a bonding, $Y_1$ represents an organic group with a valency of k+1, Rs represents a group containing at least one silicon atom, "k" represents 1, 2 or 3, and "n" represents 0 or 1.

In the following, the present invention is explained in detail, but the present invention is not limited by these.
[Tetracarboxylic Acid Diester Compound]

The tetracarboxylic acid diester compound of the present invention is a material represented by the following general formula (1),

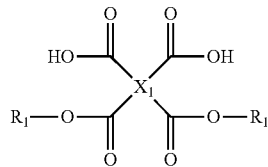
(1)

wherein, $X_1$ represents a tetravalent organic group, and $R_1$ represents a group represented by the following general formula (2),

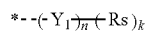
(2)

wherein, the dotted line represents a bonding, $Y_1$ represents an organic group with a valency of k+1, Rs represents a group containing at least one silicon atom, "k" represents 1, 2 or 3, and "n" represents 0 or 1.

$X_1$ in the general formula (1) is a tetravalent organic group, and it is not limited as long as it is the tetravalent organic group. It is preferably a tetravalent organic group of an alicyclic aliphatic group having 4 to 40 carbon atoms or an aromatic group, more preferably the tetravalent organic group represented by the following formula (12). The structure of $X_1$ may be one kind or a combination of two or more kinds. "The organic group" means a group containing at least one carbon atom,

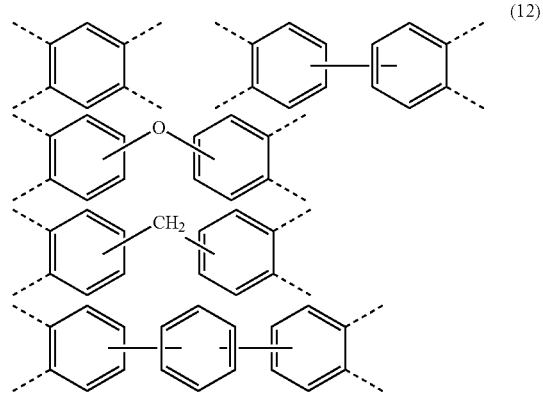
(12)

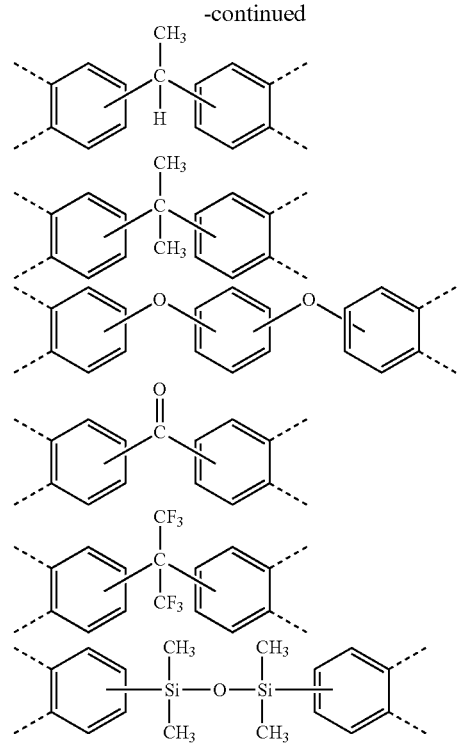

wherein, the dotted line represents a bonding.

$Y_1$ in the general formula (2) is preferably a linear or branched divalent organic group having 1 to 6 carbon atoms (for example, an alkylene group).

On the other hand, $R_1$ in the general formula (1) is preferably a group represented by the following general formula (3) or the following general formula (4),

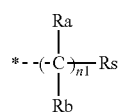
(3)

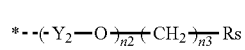
(4)

wherein, the dotted line represents a bonding, Rs represents the same meaning as before, Ra and Rb each independently represent a hydrogen atom or an alkyl group having 1 to 3 carbon atoms, $Y_2$ represents a linear or branched alkylene group having 1 to 6 carbon atoms, "n1" represents an integer of 1 to 6, "n2" represents an integer of 1 to 6 and "n3" represents an integer of 1 to 6.

In the organic group represented by the general formula (3), the organic group preferably used may be specifically mentioned the following groups, but the invention is not limited by these,

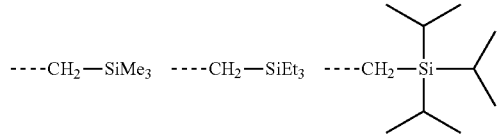

-continued

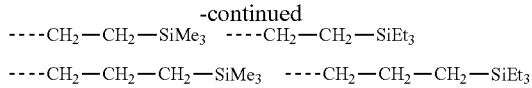
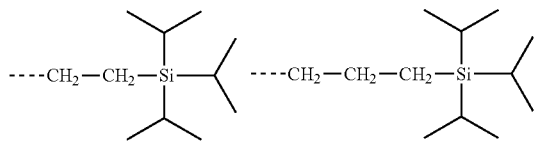

wherein, the dotted line represents a bonding.

On the other hand, when $R_1$ in the general formula (1) is the organic group represented by the general formula (4), the organic group represented by the general formula (4) is particularly preferably a group represented by the following general formula (5). If such a group is employed, solubility in an organic solvent as the developer can be sufficiently heightened,

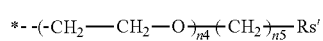 (5)

wherein, the dotted line represents a bonding, "n4" represents an integer of 1 to 6, "n5" represents an integer of 1 to 6, Rs' is a group represented by the following general formula (6),

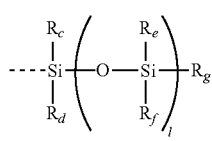 (6)

wherein, Rc to Rg each may be the same or different from each other and represent a monovalent hydrocarbon group having 1 to 8 carbon atoms, and "l" represents an integer of 1 to 100.

In the organic group represented by the general formula (4), the organic group preferably used may be specifically mentioned the following, but the invention is not limited by these,

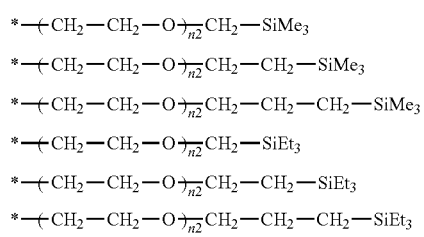

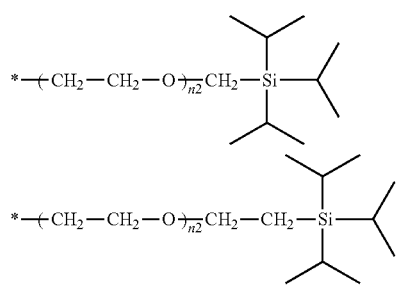

-continued

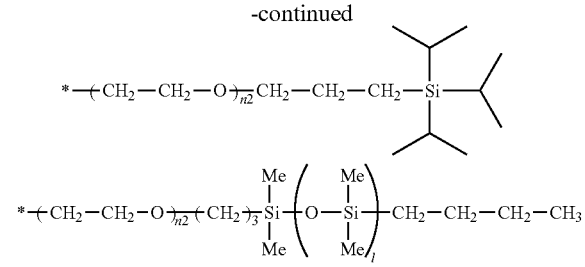

wherein, the dotted line represents a bonding, "n2" represents an integer of 1 to 6, preferably an integer of 1 to 3, more preferably an integer of 1 or 2 and most preferably 1, and "l" represents an integer of 1 to 100, preferably an integer of 1 to 30, more preferably an integer of 1 or 20 and most preferably an integer of 1 to 10.

(Method for Producing Tetracarboxylic Acid Diester Compound)

The method for producing the tetracarboxylic acid diester compound of the present invention may be mentioned a method in which the tetracarboxylic dianhydride represented by the following general formula (13) and the compound having a hydroxyl group at the terminal thereof represented by the following general formula (14) are reacted in the presence of a basic catalyst such as pyridine, etc., to introduce $R_1$ thereinto. Here, the tetracarboxylic dianhydride represented by the following general formula (13) is a material which becomes an origin of $X_1$ (for example, the tetravalent organic group represented by the formula (12)) in the general formula (1), and the compound having a hydroxyl group at the terminal thereof represented by the following general formula (14) is a material which can introduce the organic group represented by the general formula (2),

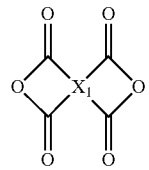 (13)

wherein, $X_1$ represents the same meaning as before,

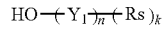 (14)

wherein, $Y_1$, Rs, "k" and "n" represent the same meanings as before.

Examples of the suitable tetracarboxylic dianhydride represented by the general formula (13) may be mentioned an aromatic dianhydride, an alicyclic dianhydride, an aliphatic dianhydride, etc. The aromatic dianhydride may be mentioned, for example, pyromellitic dianhydride, 3,3',4,4'-biphenyltetracarboxylic dianhydride, 2,3,3',4'-biphenyltetracarboxylic dianhydride, 2,3,2',3'-biphenyltetracarboxylic dianhydride, 3,3',4,4'-terphenyltetra-carboxylic dianhydride, 3,3',4,4'-oxyphthalic dianhydride, 2,3,3',4'-oxyphthalic dianhydride, 2,3,2',3'-oxyphthalic dianhydride, diphenylsulfone-3,3',4,4'-tetracarboxylic dianhydride, benzophenone-3,3',4,4'-tetracarboxylic dianhydride, 2,2-bis(3,4-dicarboxyphenyl)propane dianhydride, 2,2-bis(2,3-dicarboxyphenyl)

propane dianhydride, 1,1-bis(3,4-dicarboxyphenyl)ethane dianhydride, 1,1-bis(2,3-dicarboxyphenyl)ethane dianhydride, bis(3,4-dicarboxyphenyl)methane dianhydride, bis(2,3-dicarboxyphenyl)methane dianhydride, 1,4-(3,4-dicarboxyphenoxy)benzene dianhydride, p-phenylenebis-(trimellitic monoester acid anhydride), bis(1,3-dioxo-1,3-dihydroisobenzfuran-5-carboxylic acid)1,4-phenylene, 2,2-bis(4-(4-aminophenoxy)phenyl)propane, 1,2,5,6-naphthalene-tetracarboxylic dianhydride, 2,3,6,7-naphthalenetetra-carboxylic dianhydride, 9,9-bis(3,4-dicarboxyphenyl)-fluorene dianhydride, 2,3,5,6-pyridine tetracarboxylic dianhydride, 3,4,9,10-perylenetetracarboxylic dianhydride, 2,2-bis(3,4-dicarboxyphenyl)hexafluoropropane dianhydride, 2,2-bis(4-(3,4-dicarboxybenzoyloxy)phenyl)hexafluoropropane dianhydride, 1,6-difluoropyromellitic dianhydride, 1-trifluoromethylpyromellitic dianhydride, 1,6-ditrifluoromethylpyromellitic dianhydride, 2,2'-bis(trifluoromethyl)-4,4'-bis(3,4-dicarboxyphenoxy)biphenyl dianhydride, 2,2'-bis[(dicarboxyphenoxy)phenyl]propane dianhydride, 2,2'-bis[(dicarboxyphenoxy)phenyl]hexafluoropropane dianhydride, and an acid dianhydride compound in which these aromatic rings are substituted by an alkyl group, an alkoxy group, a halogen atom, etc., but the invention is not limited by these.

The alicyclic dianhydride may be mentioned, for example, 1,2,3,4-cyclobutanetetracarboxylic dianhydride, 1,2,3,4-cyclopentanetetracarboxylic dianhydride, 1,2,4,5-cyclohexanetetracarboxylic dianhydride, 1,2,4,5-cyclopentanetetracarboxylic dianhydride, 1,2,3,4-tetramethyl-1,2,3,4-cyclobutanetetracarboxylic dianhydride, 1,2-dimethyl-1,2,3,4-cyclobutanetetracarboxylic dianhydride, 1,3-dimethyl-1,2,3,4-cyclobutanetetracarboxylic dianhydride, 1,2,3,4-cycloheptanetetracarboxylic dianhydride, 2,3,4,5-tetrahydrofurantetracarboxylic dianhydride, 3,4-dicarboxy-1-cyclohexylsuccinic dianhydride, 2,3,5-tricarboxycyclopentylacetic dianhydride, 3,4-dicarboxy-1,2,3,4-tetrahydro-1-naphthalenesuccinic dianhydride, bicyclo[3.3.0]octane-2,4,6,8-tetracarboxylic dianhydride, bicyclo[4.3.0]nonane-2,4,7,9-tetracarboxylic dianhydride, bicyclo[4.4.0]decane-2,4,7,9-tetracarboxylic dianhydride, bicyclo[4.4.0]decane-2,4,8,10-tetracarboxylic dianhydride, tricycle[6.3.0.0<2,6>]undecane-3,5,9,11-tetracarboxylic dianhydride, bicyclo[2.2.2]octane-2,3,5,6-tetracarboxylic dianhydride, bicyclo[2.2.2]oct-7-ene-2,3,5,6-tetracarboxylic dianhydride, bicyclo[2.2.1]heptanetetracarboxylic dianhydride, bicyclo[2.2.1]heptane-5-carboxymethyl-2,3,6-tricarboxylic acid dianhydride, 7-oxabicyclo[2.2.1]heptane-2,4,6,8-tetracarboxylic dianhydride, octahydronaphthalene-1,2,6,7-tetracarboxylic dianhydride, tetradecahydroanthracene-1,2,8,9-tetracarboxylic dianhydride, 3,3',4,4'-dicyclohexanetetracarboxylic dianhydride, 3,3',4,4'-oxydicyclohexanetetracarboxylic dianhydride, 5-(2,5-dioxotetrahydro-3-furanyl)-3-methyl-3-cyclohexene-1,2-dicarboxylic anhydride, and "RIKACID" (Registered trademark) BT-100 (all tradenames, available from New Japan Chemical Co., Ltd.) and their derivatives, and an acid dianhydride compound in which these alicyclic rings are substituted by an alkyl group, an alkoxy group, a halogen atom, etc., but the invention is not limited by these.

The aliphatic dianhydride may be mentioned, for example, 1,2,3,4-butanetetracarboxylic dianhydride, 1,2,3,4-pentanetetracarboxylic dianhydride, and their derivatives, etc., but the invention is not limited by these.

These aromatic dianhydrides, alicyclic dianhydrides, or aliphatic dianhydrides may be used singly or in combination of two or more kinds.

The reaction of the tetracarboxylic dianhydride represented by the general formula (13) and the compound having a hydroxyl group at the terminal thereof represented by the general formula (14) may be carried out by mixing the tetracarboxylic dianhydride represented by the general formula (13) and the compound having a hydroxyl group at the terminal thereof represented by the general formula (14) in the presence of a basic catalyst such as pyridine, etc., in a reaction solvent at a reaction temperature of 20 to 50° C. for 4 to 10 hours under stirring and dissolution. According to the reaction, half-esterification reaction of the acid dianhydride proceeds to obtain the tetracarboxylic acid diester compound represented by the general formula (1) as a solution dissolved it in the reaction solvent.

The obtained tetracarboxylic acid diester compound may be isolated, or the obtained solution may be used as such in the next reaction with a diamine mentioned later.

The reaction solvent is preferably a material which can well dissolve the tetracarboxylic acid diester compound, and the polymer having the structural unit of the polyimide precursor obtained by the polycondensation reaction of the tetracarboxylic acid diester compound and the diamines subsequently carried out and may be mentioned, for example, N-methyl-2-pyrrolidone, N,N-dimethylacetamide, N,N-dimethylformamide, dimethylsulfoxide, tetramethylurea, γ-butyrolactone, etc. In addition, ketones, esters, lactones, ethers, halogenated hydrocarbons, hydrocarbons, etc., may be used, and there may be specifically mentioned acetone, methyl ethyl ketone, methylisobutyl ketone, cyclohexanone, methyl acetate, ethyl acetate, butyl acetate, diethyl oxalate, ethylene glycol dimethyl ether, diethylene glycol dimethyl ether, tetrahydrofuran, dichloromethane, 1,2-dichloroethane, 1,4-dichlorobutane, chlorobenzene, o-dichlorobenzene, hexane, heptane, benzene, toluene, xylene, etc. These may be used singly or in admixture of two or more kinds, if necessary.

[Polymer of Polyimide Precursor]

The polymer of a polyimide precursor (the polymer containing the structural unit of the polyimide precursor) of the present invention is a material containing the structural unit represented by the following general formula (7) (in the following, it is also referred to as a polymer containing a structural unit (7)),

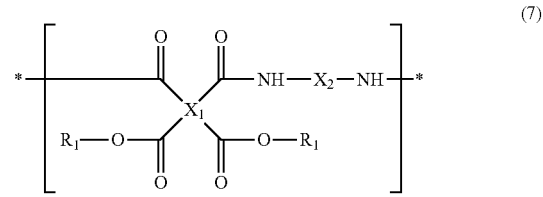

(7)

wherein, $X_1$ represents a tetravalent organic group, $X_2$ represents a divalent organic group, and $R_1$ represents a group represented by the following general formula (2),

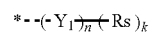

(2)

wherein, the dotted line represents a bonding, $Y_1$ represents an organic group with a valency of k+1, Rs represents a group containing at least one silicon atom, "k" represents 1, 2 or 3, and "n" represents 0 or 1.

$X_1$ and $R_1$ in the general formula (7) are the same as defined in those of the formula (1). $X_2$ in the general formula (7) is not limited as long as it is a divalent organic group, and is preferably a divalent organic group having 6 to 40 carbon atoms, more preferably a cyclic organic group containing 1 to 4 aromatic ring(s) or aliphatic rings, each having a substituent(s) or an aliphatic group having no cyclic structure or a siloxane-containing organic group. More preferred $X_2$ may be mentioned a structure represented by the following formula (15) or (16). The structure of $X_2$ may be a kind alone or a combination of two or more kinds.

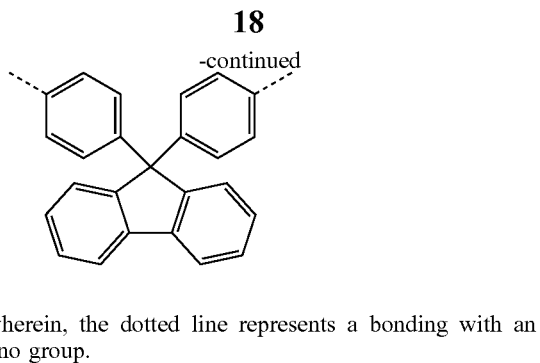

wherein, the dotted line represents a bonding with an amino group.

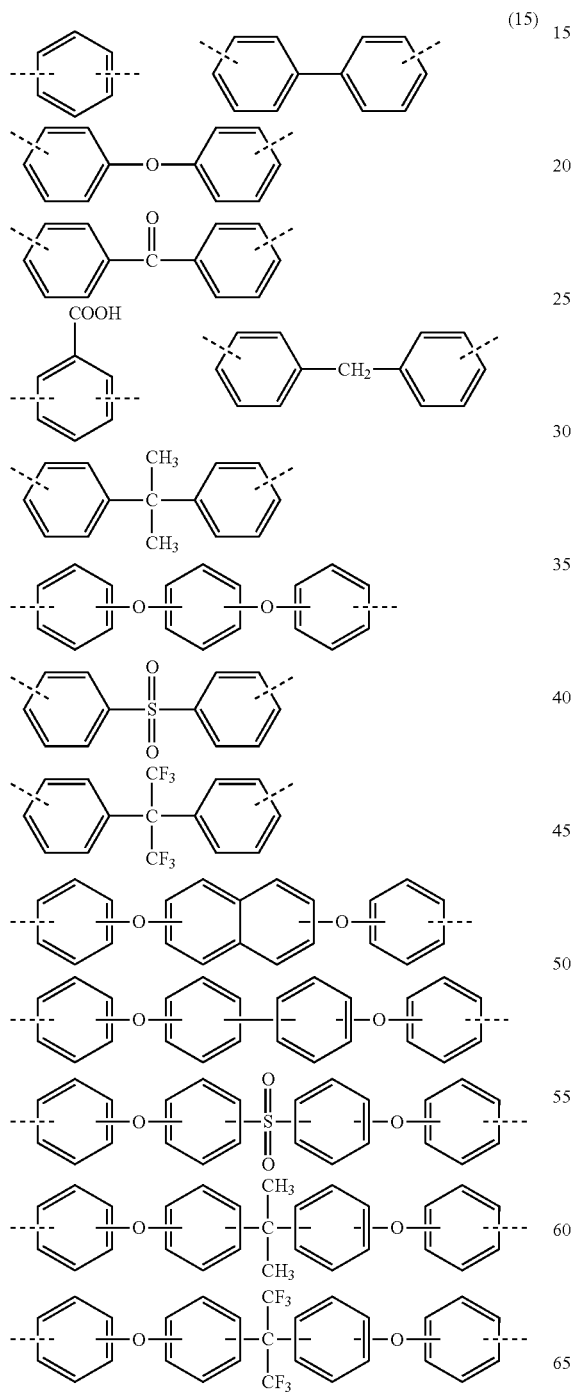

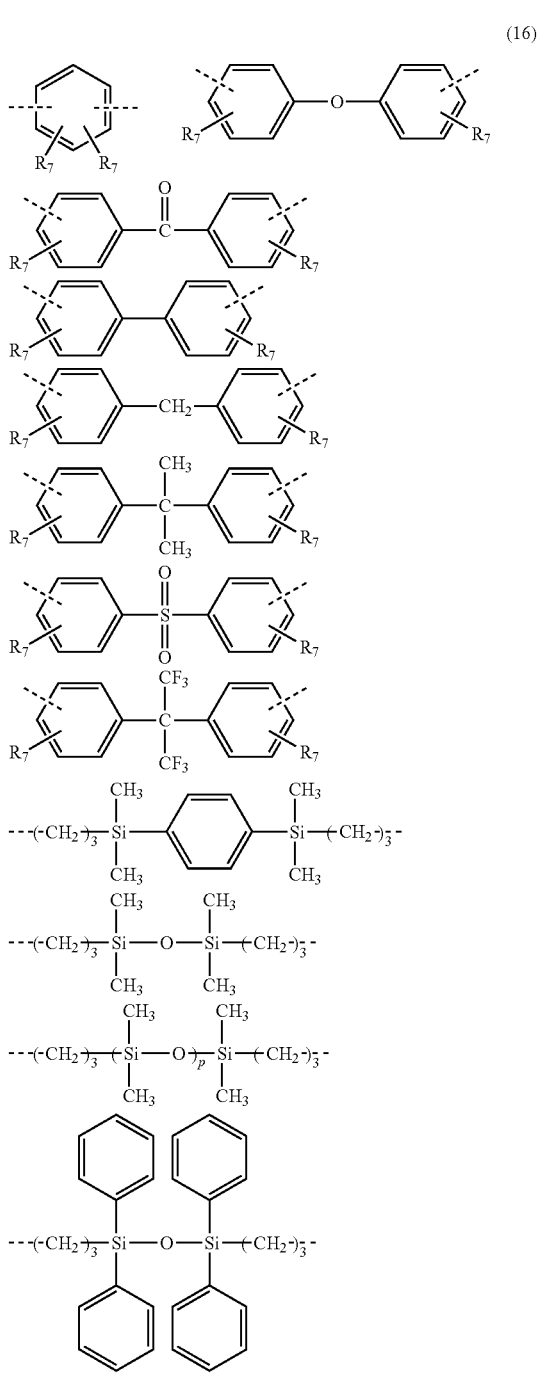

wherein, the dotted line represents a bonding with an amino group, $R_7$ each independently represents a methyl group, an ethyl group, a propyl group, an n-butyl group or a trifluoromethyl group, and p represents a positive number of 2 to 20.

The polymer of a polyimide precursor of the present invention is preferably a material further containing a structural unit represented by the following general formula (8) in addition to the structural unit represented by the general formula (7). Here, the structural unit represented by the following general formula (8) is a material having a polymerizable unsaturated bonding group represented by the following general formula (9),

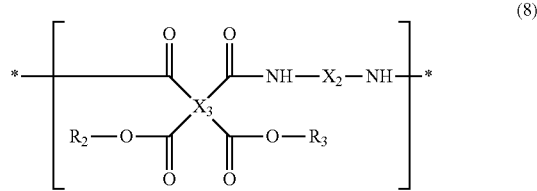
(8)

wherein, $X_2$ represents the same meaning as before, $X_3$ represents a tetravalent organic group which is the same as or different from that of the $X_1$, $R_2$ and $R_3$ each independently represent a hydrogen atom, a linear, branched or cyclic alkyl group having 1 to 6 carbon atoms, or an organic group represented by the following general formula (9), and at least one of $R_2$ and $R_3$ is an organic group represented by the following general formula (9),

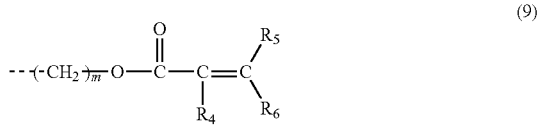
(9)

wherein, the dotted line represents a bonding, $R_4$ represents a hydrogen atom or an organic group having 1 to 3 carbon atoms, $R_5$ and $R_6$ each independently represents a hydrogen atom or an organic group having 1 to 3 carbon atoms, and "m" represents an integer of 2 to 10.

In the general formula (8), $X_3$ represents the tetravalent organic group which is the same as or different from that of the $X_1$, and it is not limited as long as it is the tetravalent organic group. $X_3$ is preferably a tetravalent organic group of an alicyclic aliphatic group having 4 to 40 carbon atoms or an aromatic group, more preferably selected from the tetravalent organic groups represented by the formula (12). Also, the structure of $X_3$ may be a kind or a combination of two or more kinds.

$R_4$ in the general formula (9) is not particularly limited as long as it is a hydrogen atom or a monovalent organic group having 1 to 3 carbon atoms, and it is preferably a hydrogen atom or a methyl group in the viewpoint of photosensitive characteristics of the negative photosensitive resin composition.

$R_5$ and $R_6$ in the general formula (9) are not particularly limited as long as they are independently a hydrogen atom or a monovalent organic group having 1 to 3 carbon atoms, and it is preferably a hydrogen atom in the viewpoint of photosensitive characteristics of the negative photosensitive resin composition.

"m" in the general formula (9) is an integer of 2 to 10, and in the viewpoint of photosensitive characteristics, it is preferably an integer of 2 to 4, and "m" is more preferably 2.

$R_2$ and $R_3$ in the general formula (8) each independently represent a hydrogen atom or a linear, branched or cyclic alkyl group having 1 to 6 carbon atoms, or the organic group represented by the general formula (9), and at least one of $R_2$ and $R_3$ is the organic group represented by the general formula (9).

(Method for Producing Polymer of Polyimide Precursor)

In the present invention, the method for producing the polymer of a polyimide precursor of the present invention is provided. The polymer of a polyimide precursor containing the structural unit represented by the general formula (7) can be obtained by reacting a tetracarboxylic acid diester compound represented by the following general formula (1) and a diamine represented by the following general formula (10),

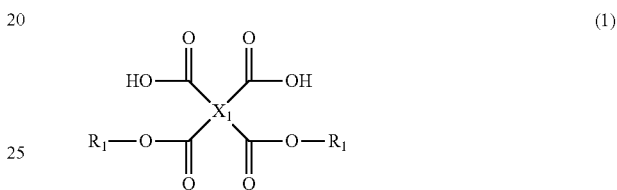
(1)

wherein, $X_1$ and $R_1$ represent the same meanings as before,

(10)

$$H_2N-X_2-NH_2$$

wherein, $X_2$ represents the same meaning as before.

The diamine represented by the general formula (10) may be mentioned an aromatic diamine, an alicyclic diamine, an aliphatic diamine, etc. Preferred aromatic diamine may be mentioned, for example, 3,4'-diaminodiphenyl ether, 4,4'-diaminodiphenyl ether, 3,4'-diaminodiphenylmethane, 4,4'-diaminodiphenylmethane, 3,3'-diaminodiphenylsulfone, 3,4'-diaminodiphenylsulfone, 4,4'-diaminodiphenylsulfone, 3,4'-diaminodiphenylsulfide, 4,4'-diaminodiphenylsulfide, 1,4-bis(4-aminophenoxy)benzene, benzidine, 2,2'-bis(trifluoromethyl)benzidine, 3,3'-bis(trifluoromethyl)benzidine, 2,2'-dimethylbenzidine, 3,3'-dimethylbenzidine, 2,2'3,3'-tetramethylbenzidine, 2,2'-dichlorobenzidine, 3,3'-dichlorobenzidine, 2,2'3,3'-tetrachlorobenzidine, m-phenylene diamine, p-phenylene diamine, 1,5-naphthalene diamine, 2,6-naphthalene diamine, bis(4-aminophenoxy-phenyl)sulfone, bis(3-aminophenoxyphenyl)sulfone, bis[4-(3-aminophenoxy)phenyl]sulfone, bis(4-aminophenoxy)biphenyl, bis{4-(4-aminophenoxy)phenyl} ether, 1,4-bis(4-aminophenoxy)benzene, 9,9-bis(4-aminophenyl)fluorene, 2,2'-bis[3-(3-aminobenzamide)-4-hydroxyphenyl]hexafluoropropane, 4-aminophenyl-4'-aminobenzoate, 4,4'-diaminobenzanilide, or a diamine compound in which these aromatic rings are substituted with an alkyl group, an alkoxy group, a halogen atom, etc., but it is not limited thereto.

The alicyclic diamine may be mentioned, for example, cyclobutane diamine, isophorone diamine, bicyclo[2.2.1]-heptanebismethylamine, tricyclo[3.3.1.1$^{3.7}$]decane-1,3-diamine, 1,2-cyclohexyldiamine, 1,3-cyclohexyldiamine, 1,4-diaminocyclohexane, trans-1,4-diaminocyclohexane, cis-1,4-diaminocyclohexane, 4,4'-diaminodicyclohexylmethane, 3,3'-dimethyl-4,4'-diaminodicyclohexylmethane, 3,3'-diethyl-4,4'-diaminodicyclohexylmethane, 3,3',5,5'-tetramethyl-4,4'-diaminodicyclohexylmethane, 3,3',5,5'-tetraethyl-4,4'-diaminodicyclohexylmethane, 3,5-diethyl-3',5'- dimethyl-4,4'-diaminodicyclohexylmethane, 4,4'-diaminodicyclohexyl ether, 3,3'-dimethyl-4,4'-diaminodicyclohexyl ether, 3,3'-diethyl-4,4'-diaminodicyclohexyl ether, 3,3',5,5'-tetramethyl-4,4'-diaminodicyclohexyl ether, 3,3',5,5'-tetraethyl-4,4'-diaminodicyclohexyl ether, 3,5-diethyl-3',5'-dimethyl-4,4'-diaminodicyclohexyl ether, 2,2-bis(4-aminocyclohexyl)propane, 2,2-bis(3-methyl-4-aminocyclo-hexyl)propane, 2,2-bis(3-ethyl-4-aminocyclohexyl)propane, 2,2-bis(3,5-dimethyl-4-aminocyclohexyl)propane, 2,2-bis(3,5-diethyl-4-aminocyclohexyl)propane, 2,2-(3,5-diethyl-3',5'-dimethyl-4,4'-diaminodicyclohexyl)propane, or a diamine compound in which these alicyclic groups are substituted with an alkyl group, an alkoxy group, a halogen atom, etc., but it is not limited thereto.

The aliphatic diamine may be mentioned, for example, alkylene diamines such as ethylenediamine, 1,3-diaminopropane, 1,4-diaminobutane, 1,5-diaminopentane, 1,6-diaminohexane, 1,7-diaminoheptane, 1,8-diaminooctane, 1,9-diaminononane, 1,10-diaminodecane, etc., ethylene glycol diamines such as bis(aminomethyl) ether, bis(2-aminoethyl) ether, bis(3-aminopropyl) ether, etc., and siloxanediamines such as 1,3-bis(3-aminopropyl)tetramethyldisiloxane, 1,3-bis(4-aminobutyl)tetramethyldisiloxane, α,ω-bis(3-aminopropyl)polydimethylsiloxane, etc., but it is not limited thereto.

These aromatic diamines, alicyclic diamines, or aliphatic diamines may be used singly or in combination of two or more kinds.

In addition, siloxanediamines are also suitably used.

Here, the polymer of a polyimide precursor containing the structural unit represented by the general formula (7) can be obtained by, for example, reacting the tetracarboxylic acid diester compound represented by the general formula (1) and the diamine represented by the general formula (10) in the presence of a dehydration condensation agent. That is, the tetracarboxylic acid diester compound represented by the general formula (1) is used for the reaction in the state of dissolving in the reaction solvent, and into the reaction solution, under ice-cooling, a known dehydration condensation agent (for example, dicyclohexylcarbodiimide, 1-ethoxycarbonyl-2-ethoxy-1,2-dihydroquinoline, 1,1-carbonyldioxy-di-1,2,3-benzotriazole, N,N'-disuccinimidyl carbonate, etc.) is added and mixed to make the tetracarboxylic acid diester compound represented by the general formula (1) a polyacid anhydride, then, the diamine represented by the general formula (10) which has separately dissolved or dispersed in a solvent is added dropwise thereto to carry out polycondensation to obtain the polymer of a polyimide precursor containing the structural unit represented by the general formula (7).

As the other method for obtaining the polymer of a polyimide precursor containing the structural unit represented by the general formula (7) by reacting the tetracarboxylic acid diester compound represented by the general formula (1) and the diamine represented by the general formula (10) (a diamine compound), there may be mentioned a synthetic method by reacting an acid chloride which is obtained by converting the tetracarboxylic acid diester compound represented by the general formula (1) by using a chlorinating agent such as thionyl chloride and dichlorooxalic acid, etc., with the diamine represented by the general formula (10).

In the reaction that the tetracarboxylic acid diester compound is converted to an acid chloride by using a chlorinating agent, a basic compound may be used. The basic compound which can be used may be mentioned, for example, pyridine, 4-dimethylaminopyridine, triethylamine, etc.

Then, the obtained acid chloride of the tetracarboxylic acid diester compound and the diamine represented by the general formula (10) are reacted in the presence of a basic catalyst to obtain the objective polymer of a polyimide precursor containing the structural unit represented by the general formula (7). At this time, the basic catalyst may be mentioned pyridine, dimethylaminopyridine, 1,8-diazabicyclo[5.4.0]undeca-7-ene, 1,5-diazabicyclo[4.3.0]nona-5-ene, etc.

Among the methods for producing the polymer of a polyimide precursor of the present invention, the solvent to be used in the method through the acid chloride is preferably a material which can well dissolve the tetracarboxylic acid diester compound and an acid chloride thereof, and also the polymer of a polyimide precursor obtained by the polycondensation reaction with diamines, and the same solvents mentioned above can be used. More specifically, there may be mentioned N-methyl-2-pyrrolidone, N,N-dimethylacetamide, N,N-dimethylformamide, dimethylsulfoxide, tetramethylurea, hexamethylphosphoric triamide, γ-butyrolactone, etc. In addition, other than the polar solvents, ketones, esters, lactones, ethers, halogenated hydrocarbons, hydrocarbons, etc., may be also used. There may be mentioned, for example, acetone, diethyl ketone, methyl ethyl ketone, methyl isobutyl ketone, cyclohexanone, methyl acetate, ethyl acetate, butyl acetate, diethyl oxalate, diethyl malonate, diethyl ether, ethylene glycol dimethyl ether, diethylene glycol dimethyl ether, tetrahydrofuran, dichloromethane, 1,2-dichloroethane, 1,4-dichlorobutane, trichloroethane, chlorobenzene, o-dichlorobenzene, hexane, heptane, octane, benzene, toluene, xylene, etc. These organic solvents may be used singly or in combination of two or more kinds.

A suitable molecular weight of the polymer of a polyimide precursor containing the structural unit represented by the general formula (7) is preferably 5,000 to 100,000, more preferably 7,000 to 30,000. If the molecular weight is 5,000 or more, it becomes easy to make a film of the negative photosensitive resin composition using the polymer of a polyimide precursor as a base resin with a desired film thickness on a substrate, while if the molecular weight is 100,000 or less, a viscosity of the negative photosensitive resin composition is not remarkably high so that there is no fear of not being able to form a film.

The polymer of a polyimide precursor containing the structural unit represented by the general formula (7), and further containing the structural unit represented by the general formula (8) can be produced by reacting the tetracarboxylic acid diester compound represented by the following general formula (1), the diamine represented by the following general formula (10) and the tetracarboxylic acid diester compound represented by the following general formula (11),

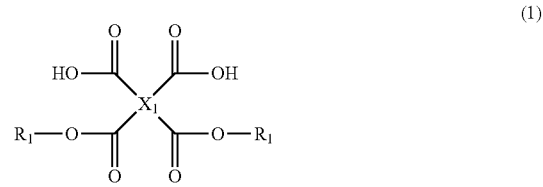

(1)

wherein, $X_1$ and $R_1$ represent the same meanings as before,

wherein, $X_2$ represents the same meaning as before,

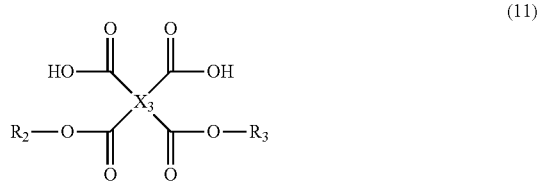

wherein, $X_3$, $R_2$, and $R_3$ represent the same meanings as before.

In the general formula (11), $X_3$ represents the tetravalent organic group which is the same as or different from that of the $X_1$, and it is not limited as long as it is the tetravalent organic group. $X_3$ is preferably a tetravalent organic group of an alicyclic aliphatic group having 4 to 40 carbon atoms or an aromatic group, more preferably selected from a tetravalent organic group represented by the formula (12). The structure of $X_3$ may be one kind or a combination of two or more kinds.

$R_2$ and $R_3$ in the general formula (11) each independently represents a hydrogen atom or a linear, branched or cyclic alkyl group having 1 to 6 carbon atoms, or the organic group represented by the general formula (9), and at least one of $R_2$ and $R_3$ is the organic group represented by the general formula (9). Here, the tetracarboxylic acid diester compound represented by the general formula (11) can be obtained by reacting the tetracarboxylic dianhydride which becomes an origin of the $X_3$ (for example, the tetravalent organic group represented by the formula (12)) and the compound having a hydroxyl group at the terminal thereof represented by the following general formula (17) in the presence of a basic catalyst such as pyridine, etc., to introduce the organic group represented by the general formula (9) into at least one of $R_2$ and $R_3$,

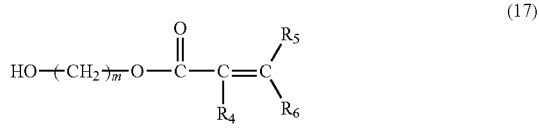

wherein, $R_4$, $R_5$, $R_6$, and "m" represent the same meanings as before.

The reaction of the tetracarboxylic dianhydride and the compound having a hydroxyl group at the terminal thereof represented by the general formula (17) may be specifically carried out in the same manner as in the reaction of the tetracarboxylic dianhydride and the compound having a hydroxyl group at the terminal thereof represented by the general formula (14) mentioned above.

$R_4$ in the general formula (17) is not limited as long as it is a hydrogen atom or an organic group having 1 to 3 carbon atoms, and it is preferably a hydrogen atom or a methyl group in the viewpoint of photosensitive characteristics of the negative photosensitive resin composition.

$R_5$ and $R_6$ in the general formula (17) are not limited as long as these are independently a hydrogen atom or an organic group having 1 to 3 carbon atoms, and preferably a hydrogen atom in the viewpoint of photosensitive characteristics of the negative photosensitive resin composition.

"m" in the general formula (17) is an integer of 2 to 10, and preferably an integer of 2 to 4 in the viewpoint of photosensitive characteristics, more preferably "m" is 2.

Among the compounds having a hydroxyl group at the terminal thereof represented by the general formula (17), suitable compound may be mentioned, for example, 2-acryloyloxyethyl alcohol, 1-acryloyloxy-3-propyl alcohol, 2-methacryoyloxyethyl alcohol, 1-methacryoyloxy-3-propyl alcohol, etc.

$R_2$ and $R_3$ in the general formula (11) may be a linear, branched or cyclic alkyl group having 1 to 6 carbon atoms. A method for introducing a linear, branched or cyclic alkyl group having 1 to 6 carbon atoms into the general formulae (8) and (11) (that is, $R_2$ and $R_3$ become a linear, branched or cyclic alkyl group having 1 to 6 carbon atoms) may be mentioned a method in which in the reaction of the compound having a hydroxyl group at the terminal thereof represented by the general formula (17) and the tetracarboxylic dianhydride carried out in the presence of a basic catalyst such as pyridine, etc., a linear, branched or cyclic alcohol having 1 to 6 carbon atoms is simultaneously charged therein.

At this time, suitable alcohol which can be used may be mentioned methanol, ethanol, 1-propanol, 2-propanol, 1-butanol, 2-butanol, 1-pentanol, 2-pentanol, 3-pentanol, neopentyl alcohol, 1-hexanol, 2-hexanol, 3-hexanol, cyclopentanol, cyclohexanol, etc.

The reaction of the tetracarboxylic acid diester compound represented by the general formula (1), the tetracarboxylic acid diester compound represented by the general formula (11) and the diamine represented by the general formula (10) may be specifically carried out in the same manner as in the reaction of the tetracarboxylic acid diester compound represented by the general formula (1) and the diamine represented by the general formula (10) mentioned above.

A molecular weight of the polymer containing a structural unit (8) is, similarly to the molecular weight of the polymer containing a structural unit (7), preferably 5,000 to 100,000, more preferably 7,000 to 30,000.

The polymer containing a structural unit (7) and the polymer containing a structural unit (8) may be sealed its both terminals by a terminal sealing agent for the purposes of controlling the molecular weight in the polycondensation reaction and suppressing change in the molecular weight with a lapse of time of the obtained polymer, i.e., suppressing gelation thereof. A terminal sealing agent which reacts with an acid dianhydride may be mentioned a monoamine or a monovalent alcohol, etc. A terminal sealing agent which reacts with a diamine compound may be mentioned an acid anhydride, a monocarboxylic acid, a monoacid chloride compound, a monoactive ester compound, dicarbonate esters, vinyl ethers, etc. In addition, various kinds of the organic groups can be introduced as a terminal group(s) by reacting the terminal sealing agent.

The monoamine to be used as a sealing agent for the terminal of the acid anhydride group may be mentioned aniline, 5-amino-8-hydroxyquinoline, 4-amino-8-hydroxyquinoline, 1-hydroxy-8-aminonaphthalene, 1-hydroxy-7-aminonaphthalene, 1-hydroxy-6-aminonaphthalene, 1-hydroxy-5-aminonaphthalene, 1-hydroxy-4-aminonaphthalene, 1-hydroxy-3-aminonaphthalene, 1-hydroxy-2-aminonaphthalene, 1-amino-7-hydroxynaphthalene, 2-hydroxy-7-aminonaphthalene, 2-hydroxy-6-aminonaphthalene, 2-hydroxy-5-aminonaphthalene, 2-hydroxy-4-aminonaphthalene, 2-hydroxy-3- aminonaphthalene, 1-amino-2-hydroxynaphthalene, 1-carboxy-8-aminonaphthalene, 1-carboxy-7-aminonaphthalene, 1-carboxy-6-aminonaphthalene, 1-carboxy-5-aminonaphthalene, 1-carboxy-4-aminonaphthalene, 1-carboxy-3-aminonaphthalene, 1-carboxy-2-aminonaphthalene, 1-amino-7-carboxynaphthalene, 2-carboxy-7-aminonaphthalene, 2-carboxy-6-aminonaphthalene, 2-carboxy-5-aminonaphthalene, 2-carboxy-4-aminonaphthalene, 2-carboxy-3-aminonaphthalene, 1-amino-2-carboxynaphthalene, 2-aminonicotinic acid, 4-aminonicotinic acid, 5-aminonicotinic acid, 6-aminonicotinic acid, 4-aminosalicylic acid, 5-aminosalicylic acid, 6-aminosalicylic acid, ameride, 2-aminobenzoic acid, 3-aminobenzoic acid, 4-aminobenzoic acid, 2-aminobenzenesulfonic acid, 3-aminobenzenesulfonic acid, 4-aminobenzenesulfonic acid, 3-amino-4,6-dihydroxypyrimidine, 2-aminophenol, 3-aminophenol, 4-aminophenol, 5-amino-8-mercaptoquinoline, 4-amino-8-mercaptoquinoline, 1-mercapto-8-aminonaphthalene, 1-mercapto-7-aminonaphthalene, 1-mercapto-6-aminonaphthalene, 1-mercapto-5-aminonaphthalene, 1-mercapto-4-aminonaphthalene, 1-mercapto-3-aminonaphthalene, 1-mercapto-2-aminonaphthalene, 1-amino-7-mercaptonaphthalene, 2-mercapto-7-aminonaphthalene, 2-mercapto-6-aminonaphthalene, 2-mercapto-5-aminonaphthalene, 2-mercapto-4-aminonaphthalene, 2-mercapto-3-aminonaphthalene, 1-amino-2-mercaptonaphthalene, 3-amino-4,6-dimercaptopyrimidine, 2-aminothiophenol, 3-aminothiophenol, 4-aminothiophenol, 2-ethynylaniline, 3-ethynylaniline, 4-ethynylaniline, 2,4-diethynylaniline, 2,5-diethynylaniline, 2,6-diethynylaniline, 3,4-diethynylaniline, 3,5-diethynylaniline, 1-ethynyl-2-aminonaphthalene, 1-ethynyl-3-aminonaphthalene, 1-ethynyl-4-aminonaphthalene, 1-ethynyl-5-aminonaphthalene, 1-ethynyl-6-aminonaphthalene, 1-ethynyl-7-aminonaphthalene, 1-ethynyl-8-aminonaphthalene, 2-ethynyl-1-aminonaphthalene, 2-ethynyl-3-aminonaphthalene, 2-ethynyl-4-aminonaphthalene, 2-ethynyl-5-aminonaphthalene, 2-ethynyl-6-aminonaphthalene, 2-ethynyl-7-aminonaphthalene, 2-ethynyl-8-aminonaphthalene, 3,5-diethynyl-1-aminonaphthalene, 3,5-diethynyl-2-aminonaphthalene, 3,6-diethynyl-1-aminonaphthalene, 3,6-diethynyl-2-aminonaphthalene, 3,7-diethynyl-1-aminonaphthalene, 3,7-diethynyl-2-aminonaphthalene, 4,8-diethynyl-1-aminonaphthalene, 4,8-diethynyl-2-aminonaphthalene, etc., but the invention is not limited by these. These may be used a single kind alone or in combination of two or more kinds.

On the other hand, the monovalent alcohol to be used as a sealing agent for the terminal of the acid anhydride group may be mentioned methanol, ethanol, 1-propanol, 2-propanol, 1-butanol, 2-butanol, 1-pentanol, 2-pentanol, 3-pentanol, 1-hexanol, 2-hexanol, 3-hexanol, 1-heptanol, 2-heptanol, 3-heptanol, 1-octanol, 2-octanol, 3-octanol, 1-nonanol, 2-nonanol, 1-decanol, 2-decanol, 1-undecanol, 2-undecanol, 1-dodecanol, 2-dodecanol, 1-tridecanol, 2-tridecanol, 1-tetradecanol, 2-tetradecanol, 1-pentadecanol, 2-pentadecanol, 1-hexadecanol, 2-hexadecanol, 1-heptadecanol, 2-heptadecanol, 1-octadecanol, 2-octadecanol, 1-nonadecanol, 2-nonadecanol, 1-eicosanol, 2-methyl-1-propanol, 2-methyl-2-propanol, 2-methyl-1-butanol, 3-methyl-1-butanol, 2-methyl-2-butanol, 3-methyl-2-butanol, 2-propyl-1-pentanol, 2-ethyl-1-hexanol, 4-methyl-3-heptanol, 6-methyl-2-heptanol, 2,4,4-trimethyl-1-hexanol, 2,6-dimethyl-4-heptanol, isononyl alcohol, 3,7-dimethyl-3-octanol, 2,4-dimethyl-1-heptanol, 2-heptylundecanol, ethylene glycol monoethyl ether, ethylene glycol monomethyl ether, ethylene glycol monobutyl ether, propylene glycol 1-methyl ether, diethylene glycol monoethyl ether, diethylene glycol monomethyl ether, diethylene glycol monobutyl ether, cyclopentanol, cyclohexanol, cyclopentanemonomethylol, dicyclopentanemonomethylol, tricyclodecanemonomethylol, norborneol, terpineol, etc., but the invention is not limited by these. These may be used a single kind alone or in combination of two or more kinds.

The acid anhydride, the monocarboxylic acid, the monoacid chloride compound and the monoactive ester compound to be used as a sealing agent for the terminal of the amino group may be mentioned an acid anhydride such as phthalic anhydride, maleic anhydride, nadic anhydride, cyclohexane dicarboxylic anhydride, 3-hydroxyphthalic anhydride, etc.; monocarboxylic acids such as 2-carboxyphenol, 3-carboxyphenol, 4-carboxyphenol, 2-carboxythiophenol, 3-carboxythiophenol, 4-carboxythiophenol, 1-hydroxy-8-carboxynaphthalene, 1-hydroxy-7-carboxynaphthalene, 1-hydroxy-6-carboxynaphthalene, 1-hydroxy-5-carboxynaphthalene, 1-hydroxy-4-carboxynaphthalene, 1-hydroxy-3-carboxynaphthalene, 1-hydroxy-2-carboxynaphthalene, 1-mercapto-8-carboxynaphthalene, 1-mercapto-7-carboxynaphthalene, 1-mercapto-6-carboxynaphthalene, 1-mercapto-5-carboxynaphthalene, 1-mercapto-4-carboxynaphthalene, 1-mercapto-3-carboxynaphthalene, 1-mercapto-2-carboxynaphthalene, 2-carboxybenzenesulfonic acid, 3-carboxybenzenesulfonic acid, 4-carboxybenzenesulfonic acid, 2-ethynylbenzoic acid, 3-ethynylbenzoic acid, 4-ethynylbenzoic acid, 2,4-diethynylbenzoic acid, 2,5-diethynylbenzoic acid, 2,6-diethynylbenzoic acid, 3,4-diethynylbenzoic acid, 3,5-diethynylbenzoic acid, 2-ethynyl-1-naphthoic acid, 3-ethynyl-1-naphthoic acid, 4-ethynyl-1-naphthoic acid, 5-ethynyl-1-naphthoic acid, 6-ethynyl-1-naphthoic acid, 7-ethynyl-1-naphthoic acid, 8-ethynyl-1-naphthoic acid, 2-ethynyl-2-naphthoic acid, 3-ethynyl-2-naphthoic acid, 4-ethynyl-2-naphthoic acid, 5-ethynyl-2-naphthoic acid, 6-ethynyl-2-naphthoic acid, 7-ethynyl-2-naphthoic acid, 8-ethynyl-2-naphthoic acid, etc., and a monoacid chloride compound in which the carboxyl group of the monocarboxylic acid is acid-chlorinated; a monoacid chloride compound in which a monocarboxyl group alone of dicarboxylic acids such as terephthalic acid, phthalic acid, maleic acid, cyclohexane dicarboxylic acid, 3-hydroxyphthalic acid, 5-norbornene-2,3-dicarboxylic acid, 1,2-dicarboxynaphthalene, 1,3-dicarboxynaphthalene, 1,4-dicarboxynaphthalene, 1,5-dicarboxynaphthalene, 1,6-dicarboxynaphthalene, 1,7-dicarboxynaphthalene, 1,8-dicarboxynaphthalene, 2,3-dicarboxynaphthalene, 2,6-dicarboxynaphthalene, 2,7-dicarboxynaphthalene, etc., is acid-chlorinated, and an active ester compound obtained by the reaction of the monoacid chloride compound and N-hydroxybenzotriazole or N-hydroxy-5-norbornene-2,3-dicarboxyimide, etc.

The dicarbonate ester compound to be used as a sealing agent for the terminal of the amino group may be mentioned di-tert-butyl dicarbonate, dibenzyl dicarbonate, dimethyl dicarbonate, diethyl dicarbonate, etc.

The vinyl ether compound to be used as a sealing agent for the terminal of the amino group may be mentioned chloroformates such as tert-butyl chloroformate, n-butyl chloroformate, isobutyl chloroformate, benzyl chloroformate, allyl chloroformate, ethyl chloroformate, isopropyl chloroformate, etc.; isocyanate compounds such as butyl isocyanate, 1-naphthyl isocyanate, octadecyl isocyanate, phenyl isocyanate, etc.; butyl vinyl ether, cyclohexyl vinyl ether, ethyl vinyl ether, 2-ethylhexyl vinyl ether, isobutyl vinyl ether, isopropyl vinyl ether, n-propyl vinyl ether, tert-butyl vinyl ether, benzyl vinyl ether, etc.

The other compounds to be used as a sealing agent for the terminal of the amino group may be mentioned benzoyl chloride, fluorenylmethyl chloroformate, 2,2,2-trichloroethyl chloroformate, methanesulfonic acid chloride, p-toluenesulfonic acid chloride, phenyl isocyanate, etc.

A ratio of the sealing agent to be introduced for the terminal of the acid anhydride group is preferably in the range of 0.1 to 60 mol % based on the tetracarboxylic dianhydride component corresponding to the general formula (13) which is a starting material of the polymer of a polyimide precursor of the present invention, particularly preferably 5 to 50 mol %, more preferably 5 to 20 mol %. A ratio of the sealing agent to be introduced for the terminal of the amino group is preferably in the range of 0.1 to 100 mol % based on the diamine component, particularly preferably 5 to 90 mol %. A plural number of different terminal groups may be introduced by reacting a plural number of the terminal sealing agents.

The polymer of a polyimide precursor of the present invention may contain a structural unit of a polyimide precursor other than the structural unit represented by general formula (7) and the structural unit represented by the general formula (8), a structural unit of a polyimide, a structural unit of a polybenzoxazole and/or a structural unit of a polybenzoxazole precursor.

[Negative Photosensitive Resin Composition]

Next, a photosensitive resin composition using the polymer of a polyimide precursor of the present invention as a base resin is explained. In the present invention, by using the polymer of a polyimide precursor of the present invention as a base resin, a negative photosensitive resin composition can be obtained. In the following, the photosensitive resin composition using the polymer of a polyimide precursor of the present invention as a base resin, specifically, the negative photosensitive resin composition capable of forming a negative type pattern and developable by an organic solvent is explained. The negative photosensitive resin composition of the present invention can be made, for example, the following three embodiments explained below but the invention is not limited by these.

The first embodiment of the negative photosensitive resin composition of the present invention is directed to a negative photosensitive resin composition which comprises
(A) a polymer of a polyimide precursor containing a structural unit represented by the general formula (8),
(B) a photo-radical initiator, and
(D) a solvent.

Component (A) in the negative photosensitive resin composition of the first embodiment is the polymer of a polyimide precursor containing the structural unit represented by the general formula (8) (that is, the polymer containing a structural unit (8)). The polymer has a polymerizable unsaturated bonding group(s) in the molecule, so that a negative photosensitive resin composition can be obtained by the combination of the polymer and the photoradical initiator.

The polymer containing a structural unit (8) of Component (A) has the structural unit represented by the general formula (7) so that it contains $R_1$. The $R_1$ has, at this time, the Rs group containing at least one silicon atom at the terminal of the substituent. In general, many of the polymers having a structural unit of the polyimide precursor have characteristics that these are not dissolved except in a polar solvent such as N-methyl-2-pyrrolidone, as in the structural unit of the polyimide precursor represented by the general formula (7) derived from the tetracarboxylic acid diester compound represented by the general formula (1), by introducing the Rs group containing at least one silicon atom at the terminal of the substituent to have the Rs group to the polymer molecule, it becomes easily soluble in a versatile organic solvent, solubility in a versatile organic solvent to be used for the development by an organic solvent is increased more and more, whereby a negative photosensitive resin composition improved in resolution can be constituted. Further, when the development by an organic solvent is carried out, worried swelling can be suppressed.

A suitable ratio of the $R_1$ to be introduced into Component (A) can be mentioned by a molar number of the $R_1$ in 100 g of Component (A). That is, a suitable introducing ratio of the $R_1$ that can be easily dissolved in a versatile organic solvent is 0.02 mol or more and 0.15 mol or less in 100 g of Component (A), more preferably 0.02 mol or more and 0.10 mol or less. An introduced amount of the $R_1$ is further preferably 0.02 mol or more and 0.05 mol or less in 100 g of Component (A). If the introduced amount of the $R_1$ is 0.02 mol or more in 100 g of Component (A), solubility to the versatile organic solvent to be used in the development by an organic solvent can be improved, and swelling can be easily suppressed. On the other hand, in the heating of post-curing after subjecting to patterning, a ring-closing reaction of imidation proceeds in the structural unit of the polyimide precursor, but the introduced $R_1$ is eliminated at the time, so that if the introduced amount of the $R_1$ is 0.15 mol or less, it is preferred since the $R_1$ becomes a plasticizer and chemical resistance of the formed film is not markedly impaired.

Component (B) in the negative photosensitive resin composition of the first embodiment is a photoradical initiator. The photoradical initiator may be optionally selected from the compounds conventionally used as the photopolymerization initiator for UV curing. The photo-radical initiator may be preferably mentioned, for example, benzophenone derivatives such as benzophenone, methyl o-benzoylbenzoate, 4-benzoyl-4'-methyl diphenyl ketone, dibenzyl ketone, fluorenone, etc.; acetophenone derivatives such as 2,2'-diethoxyacetophenone, 2-hydroxy-2-methylpropiophenone, 1-hydroxycyclohexylphenylketone, etc.; thioxanthone derivatives such as thioxanthone, 2-methylthioxanthone, 2-isopropylthioxanthone, diethylthioxanthone, etc.; benzyl derivatives such as benzyl, benzyl dimethyl ketal, benzyl-β-methoxyethyl acetal, etc.; benzoin derivatives such as benzoin, benzoin methyl ether, etc.; oximes such as 1-phenyl-1,2-butanedione-2-(O-methoxycarbonyl)oxime, 1-phenyl-1,2-propanedione-2-(O-methoxycarbonyl)oxime, 1-phenyl-1,2-propanedione-2-(O-ethoxycarbonyl)oxime, 1-phenyl-1,2-propanedione-2-(O-benzoyl)oxime, 1,3-diphenylpropanetrione-2-(O-ethoxycarbonyl)oxime, 1-phenyl-3-ethoxypropanetrione-2-(O-benzoyl)oxime, etc.; N-arylglycines such as N-phenylglycine, etc.; peroxides such as benzoylperchloride, etc.; and aromatic biimidazoles, etc., but the invention is not limited by these. These may be used a single kind alone or in admixture of two or more kinds. Among the photoradical initiators, oximes are more preferred particularly in the point of photosensitivity.

A formulation amount of Component (B) is preferably 0.1 part by mass to 20 parts by mass based on 100 parts by mass of the polymer of a polyimide precursor of Component (A) of the present invention, and more preferably 2 parts by mass to 15 parts by mass from the viewpoint of photosensitivity characteristics. The obtained negative photosensitive resin composition is excellent in photosensitivity by formulating Component (B) in an amount of 0.1 part by mass or more based on 100 parts by mass of Component (A), and on the other hand, the obtained negative photosensitive resin composition is excellent in curability with a thick film by formulating it in an amount of 20 parts by mass or less.

Next, Component (D) of the negative photosensitive resin composition in the first embodiment is a solvent. The solvent of Component (D) is not limited as long as it can dissolve Component (A) and Component (B). The solvent may be mentioned, for example, ketones such as cyclohexanone, cyclopentanone, methyl 2-n-amyl ketone, etc.; alcohols such as 3-methoxybutanol, 3-methyl-3-methoxybutanol, 1-methoxy-2-propanol, 1-ethoxy-2-propanol, etc.; ethers such as propylene glycol monomethyl ether, ethylene glycol monomethyl ether, propylene glycol monoethyl ether, ethylene glycol monoethyl ether, propylene glycol dimethyl ether, diethylene glycol dimethyl ether, etc.; esters such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, propylene glycol mono-tert-butyl ether acetate, γ-butyrolactone, etc.; and amide-based solvents such as N-methyl-2-pyrrolidone, N,N-dimethylacetamide, N,N-dimethylformamide, etc., and one or more kinds thereof can be used. In particular, preferred are ethyl lactate, cyclohexanone, cyclopentanone, propylene glycol monomethyl ether acetate, γ-butyrolactone, N-methyl-2-pyrrolidone and a mixed solvent thereof.

A formulation amount of Component (D) is preferably 50 to 2,000 parts by mass based on 100 parts by mass of the formulation amounts of Component (A) and Component (B) in total, in particular, 100 to 1,000 parts by mass is preferred.

The negative photosensitive resin composition of the first embodiment may further contain the other components than Component (A), Component (B) and Component (D). The other components may be mentioned, for example, (F) a sensitizer, an adhesion assistant, a polymerization inhibitor to heighten storage stability, (G) a surfactant commonly used to improve coatability, etc.

The sensitizer (F) may be mentioned, for example, 7-N,N-diethylaminocoumarin, 7-diethylamino-3-thenonylcoumarin, 3,3'-carbonylbis(7-N,N-diethylamino) coumarin, 3,3'-carbonylbis(7-N,N-dimethoxy) coumarin, 3-thienylcarbonyl-7-N,N-diethylaminocoumarin, 3-benzoylcoumarin, 3-benzoyl-7-N,N-methoxycoumarin, 3-(4'-methoxybenzoyl) coumarin, 3,3'-carbonylbis-5,7-(dimethoxy) coumarin, benzalacetophenone, 4'-N,N-dimethylaminobenzalacetophenone, 4'-acetaminobenzal-4-methoxyacetophenone, dimethylaminobenzophenone, diethylaminobenzophenone, 4,4'-bis(N-ethyl, N-methyl)benzophenone, etc. A content thereof is preferably 0.05 to 20 parts by mass based on 100 parts by mass of the polymer of a polyimide precursor of the present invention, more preferably 0.1 to 10 parts by mass.

The surfactant (G) is preferably a nonionic surfactant, and may be mentioned, for example, a fluorine-based surfactant, more specifically perfluoroalkyl polyoxyethylene ethanol, fluorinated alkyl ester, perfluoroalkylamine oxide, fluorine-containing organosiloxane-based compound, etc.

These surfactants which can be used are commercially available and may be mentioned, for example, Fluorad "FC-4430" (available from Sumitomo 3M Limited), Surflon "S-141" and "S-145" (all available from ASAHI GLASS CO., LTD.), UNIDYNE "DS-401", "DS-4031" and "DS-451" (all available from DAIKIN INDUSTRIES, LTD.), Megafac "F-8151" (available from DIC Corporation), "X-70-093" (available from Shin-Etsu Chemical Co., Ltd.), etc. Among these, preferred are Fluorad "FC-4430" (available from Sumitomo 3M Limited) and "X-70-093" (available from Shin-Etsu Chemical Co., Ltd.).

The second embodiment of the negative photosensitive resin composition of the present invention is directed to a negative photosensitive resin composition which comprises (A') a polymer containing a structural unit (7), or a polymer containing structural units (7) and (8),
(B) a photo-radical initiator,
(C) a crosslinking agent having two or more photo-polymerizable unsaturated bonding group in one molecule, and
(D) a solvent.

Component (A') in the negative photosensitive resin composition of the second embodiment is a polymer containing a structural unit (7), or a polymer containing structural units (7) and (8). The polymer containing a structural unit (7) is estimated to be the case where it does not have a structure which can be polymerizable or crosslinkable in the polymer molecules, so that by complementing a crosslinking agent having a photo-polymerizable unsaturated bonding group of the Component (C), it is possible to constitute a negative photosensitive resin composition of the second embodiment. On the other hand, while the polymer containing a structural unit (8) already has a polymerizable unsaturated bonding group in the molecule of the polymer, it may be complemented by newly adding a crosslinking agent.

The polymer of Component (A') contains $R_1$. The $R_1$ has the Rs group which contains at least one silicon atom at the terminal of the substituent. In general, many of the polymers having a structural unit of a polyimide precursor have characteristics that these dissolve only in a polar solvent such as N-methyl-2-pyrrolidone, the Rs group which contains at least one silicon atom at the terminal of a substituent is introduced as in the structural unit of the polyimide precursor represented by the general formula (7) derived from the tetracarboxylic acid diester compound represented by the general formula (1) to have the Rs group to the polymer molecule, it is possible to constitute a negative photosensitive resin composition which is easily soluble in a versatile organic solvent, solubility in the versatile organic solvent to be used for the development by an organic solvent is further increased and resolution is improved. Further, when the development by an organic solvent is carried out, worried swelling can be suppressed.

A suitable ratio of the $R_1$ to be introduced into Component (A') can be mentioned by a molar number of the $R_1$ in 100 g of Component (A'). That is, a suitable introducing ratio of the $R_1$ that can be easily dissolved in a versatile organic solvent is 0.02 mol or more and 0.15 mol or less in 100 g of Component (A'), more preferably 0.02 mol or more and 0.10 mol or less. An introduced amount of the $R_1$ is further preferably 0.02 mol or more and 0.05 mol or less in 100 g of Component (A'). If the introduced amount of the $R_1$ is 0.02 mol or more in 100 g of Component (A'), solubility to the versatile organic solvent to be used in the development by an organic solvent can be improved, and swelling can be easily suppressed. On the other hand, in the heating of post-curing after subjecting to patterning, a ring-closing reaction of imidation proceeds in the structural unit of the polyimide precursor, but the introduced $R_1$ is eliminated at this time, so that if the introduced amount of the $R_1$ is 0.15 mol or less, it is preferred since the $R_1$ becomes a plasticizer and chemical resistance of the formed film is not markedly impaired.

Component (B) in the negative photosensitive resin composition of the second embodiment is the photoradical initiator. The photoradical initiator of Component (B) which can be used may be mentioned the same materials as those exemplified in the first embodiment.

A formulation amount of Component (B) is preferably 0.1 part by mass to 20 parts by mass based on 100 parts by mass of the polymer of a polyimide precursor of the present invention of Component (A'), and more preferably 2 parts by mass to 15 parts by mass from the viewpoint of photosensitivity characteristics. The obtained negative photosensitive resin composition is excellent in photosensitivity by formulating Component (B) in an amount of 0.1 part by mass or more based on 100 parts by mass of Component (A'), and on the other hand, the obtained negative photosensitive resin composition is excellent in curability with a thick film by formulating it in an amount of 20 parts by mass or less.

Component (C) in the negative photosensitive resin composition of the second embodiment is a crosslinking agent having two or more photo-polymerizable unsaturated bonding group in the molecule. The crosslinking agent having two or more photo-polymerizable unsaturated bonding group in the molecule is preferably a (meth)acryl compound and may be preferably mentioned, for example, ethylene glycol diacrylate, ethylene glycol dimethacrylate, polyethylene glycol diacrylate (a number of each ethylene glycol unit of 2 to 20), polyethylene glycol dimethacrylate (a number of each ethylene glycol unit of 2 to 20), poly(1,2-propylene glycol) diacrylate, poly(1,2-propylene glycol)dimethacrylate, 1,6-hexanediol diacrylate, neopentyl glycol diacrylate, pentaerythritol diacrylate, trimethylolpropane triacrylate, pentaerythritol triacrylate, dipentaerythritol hexaacrylate, tetramethylolpropane-tetraacrylate, tetraethylene glycol diacrylate, 1,6-hexanediol dimethacrylate, neopentyl glycol dimethacrylate, pentaerythritol dimethacrylate, trimethylolpropane trimethacrylate, pentaerythritol trimethacrylate, dipentaerythritol hexamethacrylate, tetramethylolpropanetetramethacrylate, glycerol diacrylate, glycerol dimethacrylate, methylenebisacrylamide, N-methylolacrylamide, ethylene glycol diglycidyl ether-methacrylic acid adduct, glycerol diglycidyl ether-acrylic acid adduct, bisphenol A diglycidyl ether-acrylic acid adduct, bisphenol A diglycidyl ether-methacrylic acid adduct, N,N'-bis(2-methacryoyloxyethyl)urea, etc., but the invention is not limited by these.

Component (C) is preferably formulated in an amount of 1 to 100 parts by mass based on 100 parts by mass of Component (A'), more preferably in the range of 3 to 50 parts by mass. If it is in the range of 1 to 100 parts by mass, objective effects can be sufficiently obtained, and no adverse effect is exerted on developability. As the copolymerizable monomer, one kind of the compound may be used, or several kinds may be used in admixture.

Component (D) in the negative photosensitive resin composition of the second embodiment is a solvent. The solvent of Component (D) is not limited as long as it can dissolve Component (A'), Component (B) and Component (C). Component (D) may be mentioned the same materials as those exemplified in the first embodiment.

A formulation amount of Component (D) is preferably 50 to 2,000 parts by mass based on 100 parts by mass of Component (A'), Component (B) and Component (C) in total, in particular, 100 to 1,000 parts by mass is preferred.

The negative photosensitive resin composition of the second embodiment may further contain the other components than Component (A'), Component (B), Component (C) and Component (D). The other components may be mentioned the same materials as those exemplified in the first embodiment.

The third embodiment of the negative photosensitive resin composition of the present invention is a negative photosensitive resin composition comprising
(A') a polymer containing a structural unit (7), or a polymer containing structural units (7) and (8),
(B') a photoacid generator,
(C') one kind or two or more kinds of a crosslinking agent(s) selected from an amino condensate modified by formaldehyde or formaldehyde-alcohol, a phenol compound having two or more methylol groups or alkoxymethylol groups in an average in one molecule, a compound in which a hydrogen atom of a hydroxyl group of a polyvalent phenol is substituted by a glycidyl group, a compound in which a hydrogen atom of a hydroxyl group of a polyvalent phenol is substituted by a substituent represented by the following formula (C-1), and a compound containing two or more nitrogen atoms each of which has a glycidyl group(s) represented by the following formula (C-2a) or the following formula (C-2b),

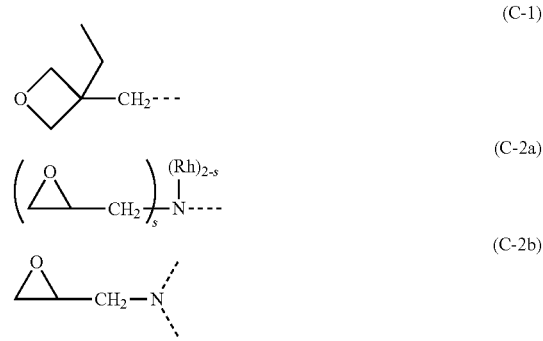

wherein, the dotted line represents a bonding, $R_h$ represents a linear, branched or cyclic alkyl group having 1 to 6 carbon atoms, and "s" represents 1 or 2, and (D) a solvent.

Component (A') of the negative photosensitive resin composition in the third embodiment is a polymer containing a structural unit (7), or a polymer containing structural units (7) and (8), and the same polymers as mentioned in the negative photosensitive resin composition of the second embodiment can be suitably used.

Component (B') of the negative photosensitive resin composition in the third embodiment is a photoacid generator. The photoacid generator which can be used may be mentioned a material which generates an acid by photoirradiation at a wavelength of 190 to 500 nm, and becomes a curing catalyst. There may be mentioned, for example, onium salts, diazomethane derivatives, glyoxime derivatives, β-ketosulfone derivatives, disulfone derivatives, nitrobenzylsulfonate derivatives, sulfonic acid ester derivatives, imid-yl-sulfonate derivatives, oximesulfonate derivatives, iminnosulfonate derivatives, triazine derivatives, etc.

The onium salts may be mentioned, for example, a compound represented by the following general formula (18),

$(R_8)_j M^+ K^-$       (18)

wherein, $R_8$ represents a linear, branched or cyclic alkyl group having 1 to 12 carbon atoms which may have a substituent(s), an aryl group having 6 to 12 carbon atoms, or an aralkyl group having 7 to 12 carbon atoms, $M^+$ represents iodonium or sulfonium, $K^-$ represents a non-nucleophilic counter ion, and "j" represents 2 or 3.

In the $R_8$, the alkyl group may be mentioned, for example, a methyl group, an ethyl group, a propyl group, a butyl group, a cyclohexyl group, a 2-oxocyclohexyl group, a norbornyl group, an adamantyl group, etc. The aryl group may be mentioned, for example, a phenyl group; an alkoxyphenyl group such as an o-, m- or p-methoxyphenyl group, an ethoxyphenyl group, m- or p-tert-butoxyphenyl group, etc.; an alkylphenyl group such as a 2-, 3- or 4-methylphenyl group, an ethylphenyl group, a 4-tert-butylphenyl group, a 4-butylphenyl group, a dimethylphenyl group, etc. The aralkyl group may be mentioned, for example, each group of a benzyl group, a phenethyl group, etc.

The non-nucleophilic counter ion of K⁻ may be mentioned a halide ion such as a chloride ion, a bromide ion, etc.; a fluoroalkyl sulfonate such as triflate, 1,1,1-trifluoroethane sulfonate, nonafluorobutane sulfonate, etc.; an aryl sulfonate such as tosylate, benzene sulfonate, 4-fluorobenzene sulfonate, 1,2,3,4,5-pentafluorobenzene sulfonate, etc.; an alkyl sulfonate such as mesylate, butane sulfonate, etc.

The diazomethane derivatives may be mentioned a compound represented by the following general formula (19),

(19)

wherein, $R_9$ may be the same or different from each other, and each represent a linear, branched or cyclic alkyl group or halogenated alkyl group having 1 to 12 carbon atoms, an aryl group or a halogenated aryl group having 6 to 12 carbon atoms, or an aralkyl group having 7 to 12 carbon atoms.

In the $R_9$, the alkyl group may be mentioned, for example, a methyl group, an ethyl group, a propyl group, a butyl group, an amyl group, a cyclopentyl group, a cyclohexyl group, a norbornyl group, an adamantyl group, etc. The halogenated alkyl group may be mentioned, for example, a trifluoromethyl group, a 1,1,1-trifluoroethyl group, a 1,1,1-trichloroethyl group, a nonafluorobutyl group, etc. The aryl group may be mentioned, for example, a phenyl group; an alkoxyphenyl group such as an o-, m- or p-methoxyphenyl group, an ethoxyphenyl group, a m- or p-tert-butoxyphenyl group, etc.; an alkylphenyl group such as a 2-, 3- or 4-methylphenyl group, an ethylphenyl group, a 4-tert-butylphenyl group, a 4-butylphenyl group, a dimethylphenyl group, etc. The halogenated aryl group may be mentioned, for example, a fluorophenyl group, a chlorophenyl group, a 1,2,3,4,5-pentafluorophenyl group, etc. The aralkyl group may be mentioned, for example, a benzyl group, a phenethyl group, etc.

Such a photoacid generator may be specifically mentioned an onium salt such as diphenyliodonium trifluoromethanesulfonate, (p-tert-butoxyphenyl)phenyliodonium trifluoromethanesulfonate, diphenyliodonium p-toluenesulfonate, (p-tert-butoxyphenyl)phenyliodonium p-toluenesulfonate, triphenylsulfonium trifluoromethanesulfonate, (p-tert-butoxyphenyl)diphenylsulfonium trifluoromethanesulfonate, bis(p-tert-butoxyphenyl)phenylsulfonium trifluoromethanesulfonate, tris(p-tert-butoxyphenyl)sulfonium trifluoromethanesulfonate, triphenylsulfonium p-toluenesulfonate, (p-tert-butoxyphenyl)diphenylsulfonium p-toluenesulfonate, bis(p-tert-butoxyphenyl)-phenylsulfonium p-toluenesulfonate, tris(p-tert-butoxyphenyl)sulfonium p-toluenesulfonate, triphenylsulfonium nonafluorobutanesulfonate, triphenylsulfonium butane-sulfonate, trimethylsulfonium trifluoromethanesulfonate, trimethylsulfonium p-toluenesulfonate, cyclohexylmethyl(2-oxocyclohexyl)sulfonium trifluoromethanesulfonate, cyclohexylmethyl(2-oxocyclohexyl)sulfonium p-toluenesulfonate, dimethylphenylsulfonium trifluoromethanesulfonate, dimethylphenylsulfonium p-toluenesulfonate, dicyclohexylphenylsulfonium trifluoromethanesulfonate, dicyclohexylphenylsulfonium p-toluenesulfonate, diphenyl(4-thiophenoxy-phenyl)sulfonium hexafluoroantimonate, etc.; diazomethane derivatives such as bis(benzenesulfonyl)diazomethane, bis(p-toluenesulfonyl)diazomethane, bis(xylenesulfonyl)-diazomethane, bis(cyclohexylsulfonyl)diazomethane, bis(cyclopentylsulfonyl)diazomethane, bis(n-butylsulfonyl)diazomethane, bis(isobutylsulfonyl) diazomethane, bis(sec-butylsulfonyl)diazomethane, bis(n-propylsulfonyl)diazomethane, bis(isopropylsulfonyl) diazomethane, bis(tert-butylsulfonyl)diazomethane, bis(n-amylsulfonyl)diazomethane, bis(isoamylsulfonyl) diazomethane, bis(sec-amylsulfonyl)diazomethane, bis(tert-amylsulfonyl)diazomethane, 1-cyclohexylsulfonyl-1-(tert-butylsulfonyl)-diazomethane, 1-cyclohexylsulfonyl-1-(tert-amylsulfonyl)-diazomethane, 1-tert-amylsulfonyl-1-(tert-butylsulfonyl)-diazomethane, etc.; glyoxime derivatives such as bis-o-(p-toluenesulfonyl)-α-dimethylglyoxime, bis-o-(p-toluenesulfonyl)-α-diphenylglyoxime, bis-o-(p-toluenesulfonyl)-α-dicyclohexylglyoxime, bis-o-(p-toluenesulfonyl)-2,3-pentanedioneglyoxime, bis-(p-toluenesulfonyl)-2-methyl-3,4-pentanedioneglyoxime, bis-o-(n-butanesulfonyl)-α-dimethylglyoxime, bis-o-(n-butanesulfonyl)-α-diphenylglyoxime, bis-o-(n-butanesulfonyl)-α-dicyclohexylglyoxime, bis-o-(n-butanesulfonyl)-2,3-pentanedioneglyoxime, bis-o-(n-butanesulfonyl)-2-methyl-3,4-pentanedioneglyoxime, bis-o-(methanesulfonyl)-α-dimethylglyoxime, bis-o-(trifluoromethanesulfonyl)-α-dimethylglyoxime, bis-o-(1,1,1-trifluoroethanesulfonyl)-α-dimethylglyoxime, bis-o-(tert-butanesulfonyl)-α-dimethylglyoxime, bis-o-(perfluorooctanesulfonyl)-α-dimethylglyoxime, bis-o-(cyclohexanesulfonyl)-α-dimethylglyoxime, bis-o-(benzenesulfonyl)-α-dimethylglyoxime, bis-o-(p-fluorobenzenesulfonyl)-α-dimethylglyoxime, bis-o-(p-tert-butylbenzenesulfonyl)-α-dimethylglyoxime, bis-o-(xylenesulfonyl)-α-dimethylglyoxime, bis-o-(camphorsulfonyl)-α-dimethylglyoxime, etc.; oximesulfonate derivatives such as α-(benzenesulfoniumoxyimino)-4-methylphenyl acetonitrile, etc.; β-ketosulfone derivatives such as 2-cyclohexylcarbonyl-2-(p-toluenesulfonyl)propane, 2-isopropylcarbonyl-2-(p-toluenesulfonyl)propane, etc.; disulfone derivatives such as diphenyldisulfone, dicyclohexyldisulfone, etc.; nitrobenzylsulfonate derivatives such as p-toluenesulfonate 2,6-dinitrobenzyl, p-toluenesulfonate 2,4-dinitrobenzyl, etc.; sulfonic acid ester derivatives such as 1,2,3-tris(methanesulfonyloxy)benzene, 1,2,3-tris(trifluoromethanesulfonyloxy)benzene, 1,2,3-tris(p-toluenesulfonyloxy)benzene, etc.; imid-yl-sulfonate derivatives such as phthalimid-yl-triflate, phthalimid-yl-tosylate, 5-norbornene-2,3-dicarboxyimid-yl-triflate, 5-norbornene-2,3-dicarboxyimid-yl-tosylate, 5-norbornene-2,3-dicarboxyimid-yl-n-butyl-sulfonate, n-trifluoromethylsulfonyloxynaphthylimide, etc.; iminosulfonates such as (5-(4-methylphenyl)sulfonyloxyimino-5H-thiophen-2-ylidene)-(2-methylphenyl)acetonitrile, (5-(4-(4-methylphenylsulfonyloxy)phenylsulfonyloxyimino)-5H-thiophen-2-ylidene)-(2-methylphenyl)-acetonitrile, etc., 2-methyl-2[(4-methylphenyl)sulfonyl]-1-[(4-methylthio)-phenyl]-1-propane, etc. Among these, imid-yl-sulfonates, iminosulfonates, oximesulfonates, etc., are suitably used. The photoacid generator may be used a single kind or in combination of two or more kinds.

A formulation amount of the photoacid generator is preferably 0.05 to 20 parts by mass based on 100 parts by mass of Component (A') in the negative photosensitive resin composition of the third embodiment of the present invention from the viewpoint of photoabsorption of the photoacid generator itself and photocurability with a thick film, particularly preferably 0.2 to 5 parts by mass.

Component (C') in the negative photosensitive resin composition of the third embodiment is one kind or two or more kinds of a crosslinking agent(s) selected from the group consisting of an amino condensate modified by formaldehyde or formaldehyde-alcohol, a phenol compound having two or more methylol groups or alkoxymethylol groups in an average in one molecule, a compound in which a hydrogen atom of a hydroxyl group of a polyvalent phenol is substituted by a glycidyl group, a compound in which a hydrogen atom of a hydroxyl group of a polyvalent phenol is substituted by a substituent represented by the following formula (C-1), and a compound containing two or more nitrogen atoms each of which has a glycidyl group(s) represented by the following formula (C-2a) or the following formula (C-2b),

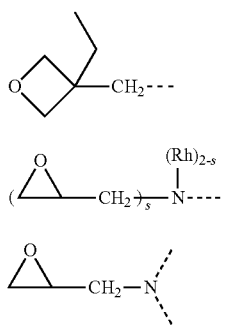

wherein, the dotted line represents a bonding, $R_h$ represents a linear, branched or cyclic alkyl group having 1 to 6 carbon atoms, and "s" represents 1 or 2.

The amino condensate modified by formaldehyde or formaldehyde-alcohol may be mentioned, for example, a melamine condensate modified by formaldehyde or formaldehyde-alcohol, or a urea condensate modified by formaldehyde or formaldehyde-alcohol.

Preparation of the melamine condensate modified by the formaldehyde or formaldehyde-alcohol may be carried out by, for example, firstly modifying a melamine monomer with formalin to methylolation according to the conventionally known method, or further modifying the resulting material with an alcohol to alkoxylation, to make a modified melamine represented by the following general formula (20). The alcohol is preferably a lower alcohol, for example, an alcohol having 1 to 4 carbon atoms.

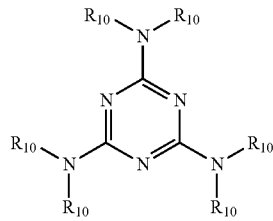

wherein, $R_{10}$ may be the same or different from each other, and each represents a methylol group, an alkoxymethyl group containing an alkoxy group having 1 to 4 carbon atoms, or a hydrogen atom, and at least one of which is a methylol group or the alkoxymethyl group.

The $R_{10}$ may be mentioned, for example, a methylol group, an alkoxymethyl group such as a methoxymethyl group, an ethoxymethyl group, etc., and a hydrogen atom, etc.

The modified melamine represented by the general formula (20) may be specifically mentioned trimethoxymethyl monomethylol melamine, dimethoxymethyl monomethylol melamine, trimethylol melamine, hexamethylol melamine, hexamethoxymethylol melamine, etc.

Then, the modified melamine represented by the general formula (20) or a multimer thereof (for example, an oligomer such as a dimer, a trimer, etc.) is subjected to addition condensation polymerization with formaldehyde according to the conventional manner until it becomes a desired molecular weight to obtain a melamine condensate modified by formaldehyde or formaldehyde-alcohol.

Preparation of the urea condensate modified by the formaldehyde or formaldehyde-alcohol may be carried out by, for example, modifying a urea condensate having a desired molecular weight with formaldehyde to methylolation according to the conventionally known method, or further modifying the resulting material with an alcohol to alkoxylation.

Specific examples of the urea condensate modified by the formaldehyde or formaldehyde-alcohol may be mentioned, for example, methoxymethylated urea condensate, ethoxymethylated urea condensate, propoxymethylated urea condensate, etc.

These modified melamine condensate and modified urea condensate may be used a single kind or two or more kinds in admixture.

Then, the phenol compound having two or more methylol groups or alkoxymethylol groups in an average in one molecule may be mentioned, for example, (2-hydroxy-5-methyl)-1,3-benzene dimethanol, 2,2',6,6'-tetramethoxymethyl bisphenol A, compounds represented by the following formulae (C-3) to (C-7), etc.

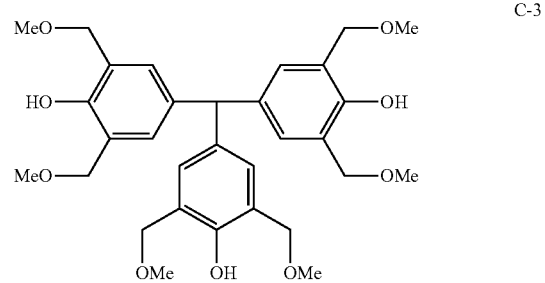

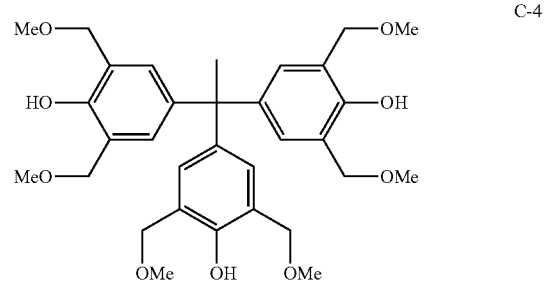

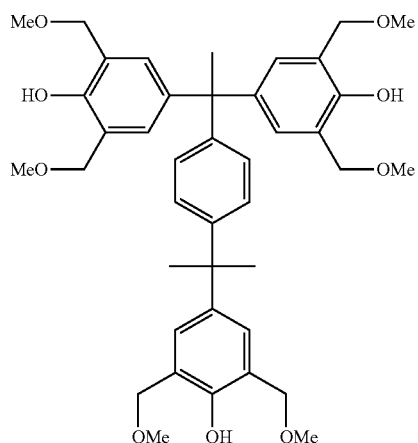

C-5

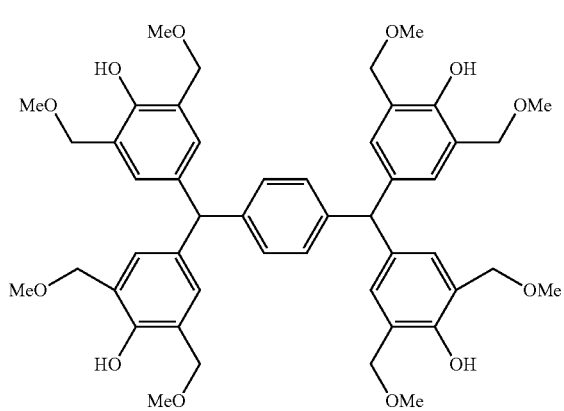

C-6

C-7

The crosslinking agent may be used a single kind or in combination of two or more kinds.

On the other hand, a compound in which a hydrogen atom of a hydroxyl group of a polyvalent phenol is substituted by a glycidyl group may be mentioned a compound obtained by reacting a hydroxyl group of bisphenol A, tris(4-hydroxyphenyl)methane or 1,1,1-tris(4-hydroxyphenyl)ethane with epichlorohydrin in the presence of a base. Suitable examples of the compound in which a hydrogen atom of a hydroxyl group of a polyvalent phenol is substituted by a glycidyl group may be mentioned compounds represented by the following formulae (C-8) to (C-14),

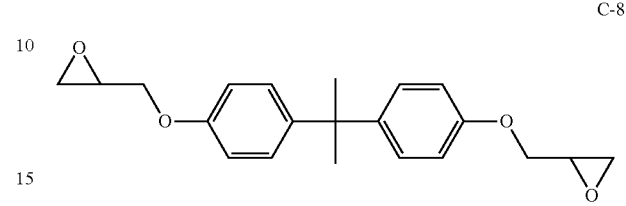

C-8

C-9

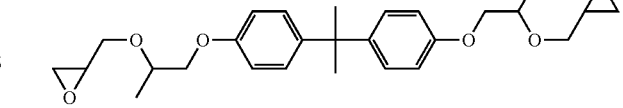

C-10

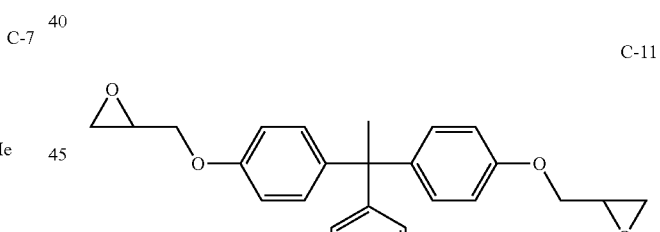

C-11

C-12

-continued

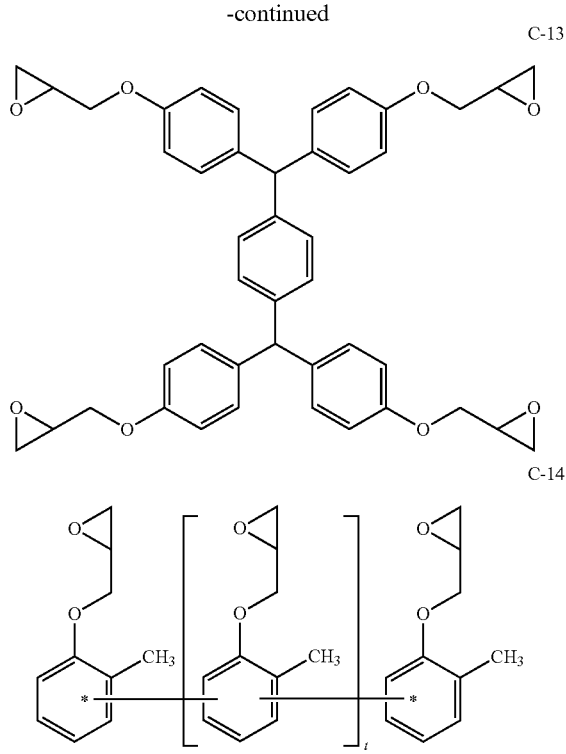
C-13

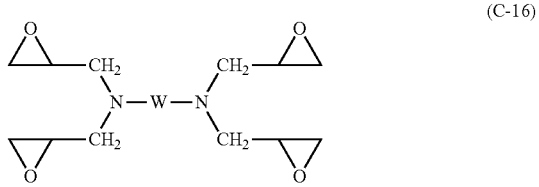
(C-2a)

wherein, the dotted line represents a bonding, Rh represents a linear, branched or cyclic alkyl group having 1 to 6 carbon atoms, and "s" represents 1 or 2,

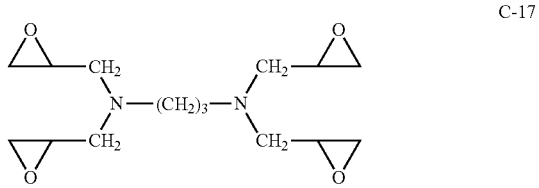
(C-16)

wherein, W represents a linear, branched or cyclic alkylene group having 2 to 12 carbon atoms, or a divalent aromatic group.

The compound represented by the formula (C-16) may be exemplified by, for example, compounds represented by the following formulae (C-17) to (C-20).

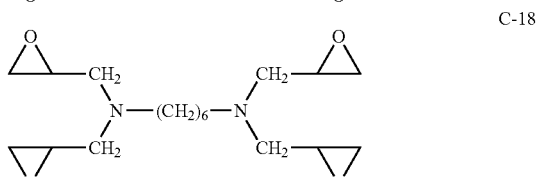
C-17

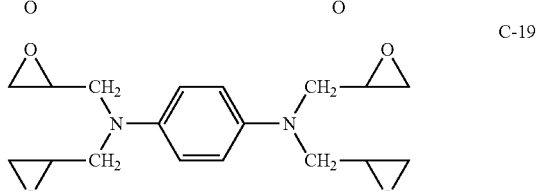
C-18

C-14

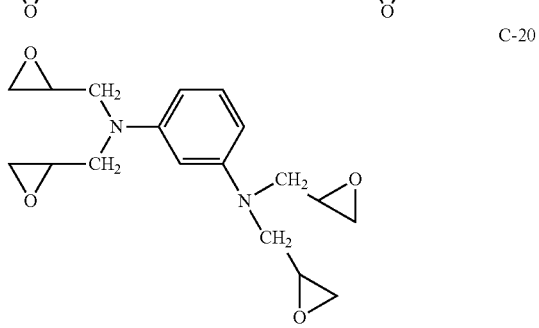
C-19 wherein, "t" is 2≤t≤3.

These compounds in which a hydrogen atom of a hydroxyl group of a polyvalent phenol has been substituted by a glycidoxy group may be used as a crosslinking agent with a single kind or two or more kinds in combination.

The compound in which a hydrogen atom of a hydroxyl group of a polyvalent phenol is substituted by a substituent represented by the following formula (C-1) may be mentioned a compound having two or more of the substituents and represented by the following formula (C-15),

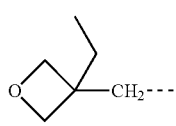
(C-1)

wherein, the dotted line represents a bonding,

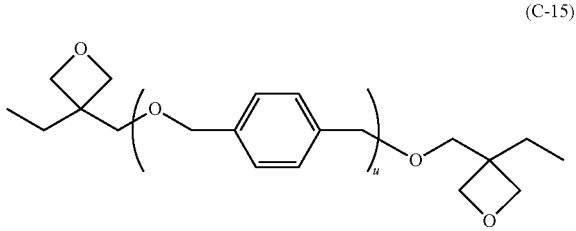
(C-15)

C-20 wherein, "u" is 1≤u≤3.

On the other hand, the compound containing two or more nitrogen atoms each of which has a glycidyl group(s) represented by the following formula (C-2a) may be mentioned a compound represented by the following formula (C-16), On the other hand, as the compound containing two or more nitrogen atoms each of which has a glycidyl group(s) represented by the following formula (C-2b), the compound represented by the following formula (C-21) may be suitably used.

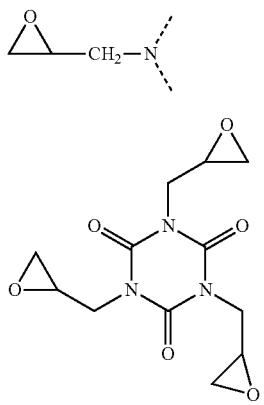

(C-2b)

(C-21)

The compound containing two or more nitrogen atoms each of which has a glycidyl group(s) represented by the formula (C-2a) or (C-2b) may be used as a crosslinking agent with a single kind or two or more kinds in combination.

Component (C') is a component to cause a crosslinking reaction with the polymer of a polyimide precursor of the present invention to carry out patterning easily as well as a component to further heighten strength of the cured product. A weight average molecular weight of such a Component (C') is preferably 150 to 10,000 from the viewpoints of photocurability and heat resistance, and in particular, those having 200 to 3,000 are preferred.

A formulation amount of Component (C') is preferably 0.5 to 50 parts by mass based on 100 parts by mass of Component (A') in the negative photosensitive resin composition of the third embodiment of the present invention, and in particular, 1 to 30 parts by mass is preferred.

The solvent of Component (D) in the negative photosensitive resin composition of the third embodiment may be mentioned those similar to the solvents explained in the negative photosensitive resin composition of the first and the second embodiments as suitable solvents.

The negative photosensitive resin composition of the third embodiment may further contain the other components than Component (A'), Component (B'), Component (C'), and Component (D). The other components may be mentioned, for example, (F) a sensitizer, an adhesion assistant, a polymerization inhibitor to heighten storage stability, (G) a surfactant to be added for the purpose of improving coating property, etc., and as (F) the sensitizer and (G) the surfactant, those compounds, etc., exemplified above are suitably used.

In the negative photosensitive resin composition of the third embodiment, a basic compound may be added as Component (H), if necessary. The basic compound is suitably a compound which can suppress a diffusion rate of the acid generated from the photoacid generator to be diffused in the resist film. By formulating the basic compound, resolution can be improved, change in sensitivity after exposure can be suppressed, a substrate or environment dependency can be reduced, and exposure margin or pattern profile, etc., can be improved.

The basic compound may be mentioned primary, secondary and tertiary aliphatic amines, mixed amines, aromatic amines, hetrocyclic amines, a nitrogen-containing compound having a carboxyl group, a nitrogen-containing compound having a sulfonyl group, a nitrogen-containing compound having a hydroxyl group, a nitrogen-containing compound having a hydroxyphenyl group, an alcoholic nitrogen-containing compound, amide derivatives, imide derivatives, and further a compound represented by the following general formula (21), etc., $$N(\alpha)_q(\beta)_{3-q} \tag{21}$$

wherein, "q" is 1, 2 or 3, a side chain α's may be the same or different from each other, and each represents any of the substituent represented by the following general formulae (22) to (24), a side chain β may be the same or different from each other, and each represents a hydrogen atom, or a linear, branched or cyclic alkyl group having 1 to 20 carbon atoms, which may contain an ether bond or a hydroxyl group, and the side chains a may be bonded to form a ring,

(22)

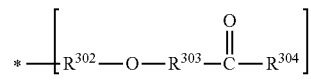

(23)

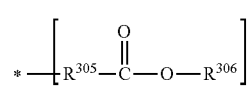

(24)

Here, each of $R^{300}$, $R^{302}$ and $R^{305}$ independently represent a linear or branched alkylene group having 1 to 4 carbon atoms, each of $R^{301}$ and $R^{304}$ independently represent a hydrogen atom or a linear, branched or cyclic an alkyl group having 1 to 20 carbon atoms, and may contain one or a plural number of a hydroxyl group(s), an ether bond(s), an ester bond(s) or a lactone ring(s), $R^{303}$ represents a single bond or a linear or branched alkylene group having 1 to 4 carbon atoms, $R^{306}$ represents a linear, branched or cyclic alkyl group having 1 to 20 carbon atoms, and may contain one or a plural number of a hydroxyl group(s), an ether bond(s), an ester bond(s) or a lactone ring(s), and * represents a bonging terminal.

The primary aliphatic amines may be exemplified by, for example, ammonia, methylamine, ethylamine, n-propylamine, isopropylamine, n-butylamine, isobutylamine, sec-butylamine, tert-butylamine, pentylamine, tert-amylamine, cyclopentylamine, hexylamine, cyclohexylamine, heptylamine, octylamine, nonylamine, decylamine, dodecylamine, cetyl-amine, methylenediamine, ethylenediamine, tetraethylene-pentamine, etc.

The secondary aliphatic amines may be exemplified by, for example, dimethylamine, diethylamine, di-n-propylamine, diisopropylamine, di-n-butylamine, diisobutylamine, di-sec-butylamine, dipentylamine, dicyclopentylamine, dihexylamine, dicyclohexylamine, diheptylamine, dioctylamine, dinonylamine, didecylamine, didodecylamine, dicetylamine, N,N-dimethylmethylenediamine, N,N-dimethylethylenediamine, N,N-dimethyltetraethylenepentamine, etc.

The tertiary aliphatic amines may be exemplified by, for example, trimethylamine, triethylamine, tri-n-propylamine, triisopropylamine, tri-n-butylamine, triisobutyl-amine, tri-sec-butylamine, tripentylamine, tricyclopentyl-amine, trihexylamine, tricyclohexylamine, triheptylamine, trioctylamine, trinonylamine, tridecylamine, tridodecyl-amine, tricetylamine, N,N,N',N'-tetramethylmethylene-diamine, N,N,N',N'-tetramethylethylenediamine, N,N,N',N'-tetramethyltetraethylenepentamine, etc.

The mixed amines may be exemplified by, for example, dimethylethylamine, methylethylpropylamine, benzylamine, a phenethyl amine, benzyldimethylamine, etc.

The aromatic amines and the heterocyclic amines may be exemplified by, for example, aniline derivatives (for example, aniline, N-methylaniline, N-ethylaniline, N-propylaniline, N,N-dimethylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline, N,N-dimethyltoluidine, etc.), diphenyl(p-tolyl)amine, methyldiphenylamine, triphenyl-amine, phenylenediamine, naphthylamine, diaminonaphthalene, pyrrole derivatives (for example, pyrrole, 2H-pyrrole, 1-methylpyrrole, 2,4-dimethylpyrrole, 2,5-dimethylpyrrole, N-methylpyrrole, etc.), oxazole derivatives (for example, oxazole, isoxazole, etc.), thiazole derivatives (for example, thiazole, isothiazole, etc.), imidazole derivatives (for example, imidazole, 4-methylimidazole, 4-methyl-2-phenylimidazole, etc.), pyrazole derivatives, furazan derivatives, pyrroline derivatives (for example, pyrroline, 2-methyl-1-pyrroline, etc.), pyrrolidine derivatives (for example, pyrrolidine, N-methylpyrrolidine, pyrrolidinone, N-methylpyrrolidone, etc.), imidazoline derivatives, imidazolidine derivatives, pyridine derivatives (for example, pyridine, methylpyridine, ethylpyridine, propylpyridine, butylpyridine, 4-(1-butylpentyl) pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 1-methyl-2-pyridine, 4-pyrrolidinopyridine, 1-methyl-4-phenylpyridine, 2-(1-ethylpropyl)pyridine, aminopyridine, dimethylaminopyridine, etc.), pyridazine derivatives, pyrimidine derivatives, pyrazine derivatives, pyrazoline derivatives, pyrazolidine derivatives, piperidine derivatives, piperadine derivatives, morpholine derivatives, indole derivatives, isoindole derivatives, 1H-indazole derivatives, indoline derivatives, quinoline derivatives (for example, quinoline, 3-quinolinecarbonitrile, etc.), isoquinoline derivatives, cinnoline derivatives, quinazoline derivatives, quinoxaline derivatives, phthalazine derivatives, purine derivatives, puteridine derivatives, carbazole derivatives, phenanthridine derivatives, acridine derivatives, phenazine derivatives, 1,10-phenanthroline derivatives, adenine derivatives, adenosine derivatives, guanine derivatives, guanosine derivatives, uracil derivatives, uridine derivatives, etc.

The nitrogen-containing compound having a carboxyl group may be exemplified by, for example, aminobenzoic acid, indolecarboxylic acid, amino acid derivatives (for example, nicotinic acid, alanine, arginine, aspartic acid, glutamic acid, glycine, histidine, isoleucine, glycyrleucine, leucine, methionine, phenylalanine, threonine, lysine, 3-aminopyrazine-2-carboxylic acid, methoxyalanine, etc.), etc.

The nitrogen-containing compound having a sulfonyl group may be exemplified by, for example, 3-pyridine sulfonic acid, pyridinium p-toluenesulfonate, etc.

The nitrogen-containing compound having a hydroxyl group, the nitrogen-containing compound having a hydroxyphenyl group and the alcoholic nitrogen-containing compound may be exemplified by, for example, 2-hydroxypyridine, aminocresol, 2,4-quinolinediol, 3-indolemethanol hydrate, monoethanolamine, diethanolamine, triethanolamine, N-ethyldiethanolamine, N,N-diethylethanolamine, triisopropanolamine, 2,2'-iminodiethanol, 2-aminoethanol, 3-amino-1-propanol, 4-amino-1-butanol, 4-(2-hydroxyethyl)morpholine, 2-(2-hydroxyethyl)pyridine, 1-(2-hydroxyethyl)piperadine, 1-[2-(2-hydroxyethoxy)ethyl]piperadine, piperidineethanol, 1-(2-hydroxyethyl)pyrrolidine, 1-(2-hydroxyethyl)-2-pyrrolidinone, 3-piperidino-1,2-propanediol, 3-pyrrolidino-1,2-propanediol, 8-hydroxyjulolidine, 3-quinuclidinol, 3-tropanol, 1-methyl-2-pyrrolidineethanol, 1-aziridine ethanol, N-(2-hydroxyethyl)phthalimide, N-(2-hydroxyethyl) isonicotinamide, etc.

The amide derivatives may be exemplified by, for example, formamide, N-methylformamide, N,N-dimethylformamide, acetamide, N-methylacetamide, N,N-dimethylacetamide, propionamide, benzamide, etc.

The imide derivatives may be exemplified by, for example, phthalimide, succinimide, maleimide, etc.

The compound represented by the general formula (21) may be exemplified by, for example, tris[2-(methoxymethoxy)ethyl]amine, tris[2-(2-methoxyethoxy)ethyl]amine, tris[2-(2-methoxyethoxymethoxy)ethyl]amine, tris[2-(1-methoxyethoxy)ethyl]amine, tris[2-(1-ethoxyethoxy)ethyl]-amine, tris[2-(1-ethoxyoxopropoxy)ethyl]amine, tris[2-{2-(2-hydroxyethoxy)ethoxy}ethyl]amine, 4,7,13,16,21,24-hexaoxa-1,10-diazabicyclo[8.8.8]hexacosane, 4,7,13,18-tetraoxa-1,10-diazabicyclo[8.5.5]eicosane, 1,4,10,13-tetraoxa-7,16-diazabicyclooctadecane, 1-aza-12-crown-4, 1-aza-15-crown-5, 1-aza-18-crown-6, tris(2-formyloxyethyl)-amine, tris(2-acetoxyethyl)amine, tris(2-propionyloxy-ethyl)amine, tris(2-butyryloxyethyl)amine, tris(2-isobutyryloxyethyl)amine, tris(2-valeryloxyethyl)amine, tris(2-pivaloyloxyethyl)amine, N,N-bis(2-acetoxyethyl)2-(acetoxyacetoxy)ethylamine, tris(2-methoxycarbonyloxyethyl)amine, tris(2-tert-butoxycarbonyloxyethyl)amine, tris[2-(2-oxopropoxy)ethyl]amine, tris[2-(methoxycarbonylmethyl)oxyethyl]amine, tris[2-(tert-butoxycarbonylmethyloxy)ethyl]amine, tris[2-(cyclohexyloxycarbonylmethyloxy)-ethyl]amine, tris(2-methoxycarbonylethyl)amine, tris(2-ethoxycarbonylethyl)amine, N,N-bis(2-hydroxyethyl)2-(methoxycarbonyl)ethylamine, N,N-bis(2-acetoxyethyl)2-(methoxycarbonyl)ethylamine, N,N-bis(2-hydroxyethyl)2-(ethoxycarbonyl)ethylamine, N,N-bis(2-acetoxyethyl)2-(ethoxycarbonyl)ethylamine, N,N-bis(2-hydroxyethyl)2-(2-methoxyethoxycarbonyl)ethylamine, N,N-bis(2-acetoxyethyl)2-(2-methoxyethoxycarbonyl)ethylamine, N,N-bis(2-hydroxyethyl)2-(2-hydroxyethoxycarbonyl)ethylamine, N,N-bis(2-acetoxyethyl)2-(2-acetoxyethoxycarbonyl)ethylamine, N,N-bis(2-hydroxyethyl)2-[(methoxycarbonyl)methoxycarbonyl]-ethylamine, N,N-bis(2-acetoxyethyl)2-[(methoxycarbonyl)-methoxycarbonyl]ethylamine, N,N-bis(2-hydroxyethyl)2-(2-oxopropoxycarbonyl)ethylamine, N,N-bis(2-acetoxyethyl)2-(2-oxopropoxycarbonyl)ethylamine, N,N-bis(2-hydroxyethyl)2-(tetrahydrofurfuryloxycarbonyl)ethylamine, N,N-bis(2-acetoxyethyl)2-(tetrahydrofurfuryloxycarbonyl)ethylamine, N,N-bis(2-hydroxyethyl)2-[(2-oxotetrahydrofuran-3-yl)-oxycarbonyl]ethylamine, N,N-bis(2-acetoxyethyl)2-[(2-oxotetrahydrofuran-3-yl)oxycarbonyl]ethylamine, N,N-bis(2-hydroxyethyl)2-(4-hydroxybutoxycarbonyl)ethylamine, N,N-bis(2-formyloxyethyl)2-(4-formyloxybutoxycarbonyl)ethylamine, N,N-bis(2-formyloxyethyl)2-(2-formyloxyethoxy-carbonyl)ethylamine, N,N-bis(2-methoxyethyl)2-(methoxycarbonyl)ethylamine, N-(2-hydroxyethyl)bis[2-(methoxycarbonyl)ethyl]amine, N-(2-acetoxyethyl)bis[2-(methoxycarbonyl)ethyl]amine, N-(2-hydroxyethyl)bis[2-(ethoxy-carbonyl)ethyl]amine, N-(2-acetoxyethyl)bis[2-(ethoxy-carbonyl)ethyl]amine, N-(3-hydroxy-1-propyl)bis[2-(methoxycarbonyl)ethyl]amine, N-(3-acetoxy-1-propyl)

bis[2-(methoxycarbonyl)ethyl]amine, N-(2-methoxyethyl) bis[2-(methoxycarbonyl)ethyl]amine, N-butylbis[2-(methoxycarbonyl)ethyl]amine, N-butylbis[2-(2-methoxyethoxycarbonyl)ethyl]amine, N-methylbis(2-acetoxyethyl)amine, N-ethylbis(2-acetoxyethyl)amine, N-methylbis(2-pivaloyloxyethyl)amine, N-ethylbis[2-(methoxycarbonyloxy)ethyl]amine, N-ethylbis[2-(tert-butoxycarbonyloxy)ethyl]amine, tris(methoxycarbonylmethyl)amine, tris(ethoxycarbonylmethyl)amine, N-butylbis(methoxycarbonylmethyl)amine, N-hexylbis(methoxycarbonylmethyl)amine, β-(diethylamino)-δ-valerolactone, and the invention is not limited by these. The basic compound may be used a single kind or in combination of two or more kinds.

A formulation amount of the basic compound is preferably 0 to 3 parts by mass based on 100 parts by mass of Component (A') in the negative photosensitive resin composition of the third embodiment of the present invention in the viewpoint of sensitivity, particularly preferably 0.01 to 1 part by mass.

In the negative photosensitive resin composition of the present invention, the preparation thereof is carried out by the usual method. The respective components are mixed under stirring, and then, the mixture is filtered by a filter, etc., to prepare the negative photosensitive resin composition.

(Patterning Process)

Next, the patterning process using the negative photosensitive resin composition of the present invention is explained.

For forming a pattern of the negative photosensitive resin composition of the present invention, it may be carried out by employing a conventionally known lithography technology and, for example, by coating a negative photosensitive resin composition onto a silicon wafer or a $SiO_2$ substrate, a SiN substrate, or a substrate onto which a pattern of copper wiring, etc., has been formed with a manner of spin coating (a spin coating method) and pre-baking under the conditions of 80 to 130° C. for 50 to 600 seconds to form a film of a photosensitive material having a thickness of 1 to 50 μm, preferably 1 to 30 μm, more preferably 5 to 20 μm.

In the spin coating method, the negative photosensitive resin composition is dispensed onto the silicon substrate with an amount of 5 mL or so, and then, the substrate is rotated to be able to coat the negative photosensitive resin composition onto the substrate. At this time, it is easily possible to adjust the thickness of the film of the photosensitive material on the substrate by adjusting the rotation speed thereof.

Then, a mask for forming the objective pattern is holding over the film of the photosensitive material and a high energy beam such as i-line, g-line, etc., having a wavelength of 190 to 500 nm or an electron beam is irradiated thereto with an exposure dose of 1 to 5,000 $mJ/cm^2$ or so, preferably 100 to 2,000 $mJ/cm^2$ or so.

Next, if necessary, it may be subjected to heating after exposure (post exposure bake (PEB)) on a hot plate at 60 to 150° C. for 1 to 10 minutes, preferably at 80 to 120° C. for 1 to 5 minutes.

Thereafter, development is carried out. In the negative photosensitive resin composition of the first embodiment, the second embodiment and the third embodiment of the present invention, development by an organic solvent is possible in either of the compositions.

A suitable organic solvent which can be used for the development by an organic solvent may be mentioned those of the solvents used in the preparation of the negative photosensitive resin composition of the present invention. It is preferably mentioned, for example, ketones such as cyclohexanone, cyclopentanone, etc., and further glycol such as propylene glycol monomethyl ether, etc. The development may be carried out by the usual method such as a spray method, a paddle method, etc., or by dipping in the developer, etc. Thereafter, a resist film having a desired pattern can be obtained by subjecting to washing, rinsing, drying, etc., if necessary.

The film having a pattern, which is obtained by the patterning process, is heated at a temperature of 100 to 300° C., preferably 150 to 300° C., more preferably 180 to 250° C., using an oven or a hot plate to carry out heating and post-curing to form a cured film. During the post-curing, imide ring-closing reaction occurs at the structural unit of the polyimide precursor of the polymer of a polyimide precursor of the present invention, and the Rs group which contains at least one silicon atom is eliminated. If the post-curing temperature is 100 to 300° C., crosslinking density of the film of the negative photosensitive resin composition can be increased and the remaining volatile component can be removed, so that it is preferred from the viewpoints of adhesiveness to the substrate, heat resistance or strength, and further electric characteristics. The post-curing time can be made 10 minutes to 10 hours.

The formed pattern is used as a protective film which covers a wiring, a circuit and a substrate, etc., these formed patterns and protective films show excellent adhesiveness to wirings to be coated, a metal layer such as Cu of a circuit, on a metal electrode existing on the substrate or on an insulating substrate such as SiN existing in wirings to be coated or circuits while maintaining excellent insulating property, and further resolution performance to realize fine patterning can be markedly improved while maintaining mechanical strength suitable as a protective film.

The cured film thus obtained is excellent in adhesiveness to the substrate, heat resistance, electric characteristics, mechanical strength and chemical resistance to an alkaline peeling liquid, etc., excellent in reliability of a semiconductor device using it as a film for protection, in particular, it can prevent from generating cracks at the time of a temperature cycle test, whereby it can be suitably used as a film for protection of electric and electronic parts, and a semiconductor device, etc.

The film for protection is effective for an insulating film for a semiconductor device including rewiring use, an insulating film for a multilayer printed board, a solder mask, a use for a coverlay film, etc., due to its heat resistance, chemical resistance and insulating property.

EXAMPLES

In the following, the present invention is more specifically explained by referring to Synthesis Examples, Comparative Synthesis Examples, Examples and Comparative examples, but the present invention is not limited by these examples mentioned below.

I. Synthesis of Polymer of Polyimide Precursor

Chemical structures of the compounds used in the following Synthesis Examples are mentioned below.

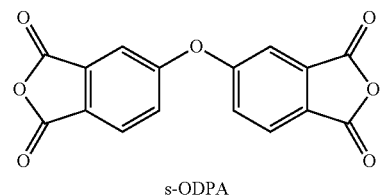

s-ODPA

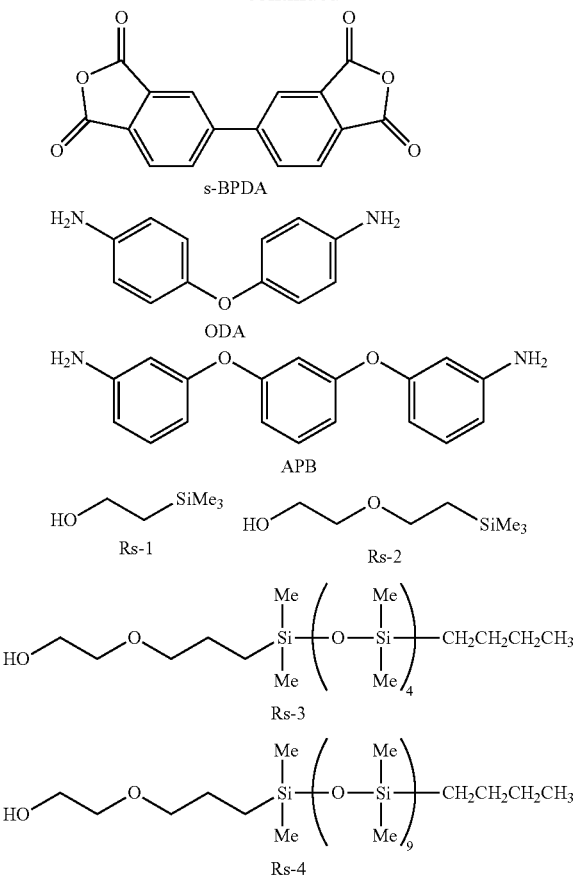

[Synthesis Example 1] Synthesis of Tetracarboxylic Acid Diester Compound (X-1)

In a 3 L of a flask equipped with a stirrer and a thermometer were charged 100 g (340 mmol) of 3,3',4,4'-biphenyltetracarboxylic dianhydride (s-BPDA), 68.8 g (680 mmol) of triethylamine, 41.5 g (340 mmol) of N,N-dimethyl-4-aminopyridine and 400 g of γ-butyrolactone, then, 80.4 g (680 mmol) of 2-(trimethylsilyl)ethanol (Rs-1) was added dropwise to the mixture while stirring at room temperature, and the resulting mixture was stirred under room temperature for 24 hours. Thereafter, under ice-cooling, 408 g of 10% aqueous hydrochloric acid solution was added dropwise to stop the reaction. To the reaction mixture was added 800 g of 4-methyl-2-pentanone, and the organic layer was collected by separation and washed with 600 g of water six times. The solvent of the obtained organic layer was distilled off to obtain 171 g of the tetracarboxylic acid diester compound (X-1) having the following structure.

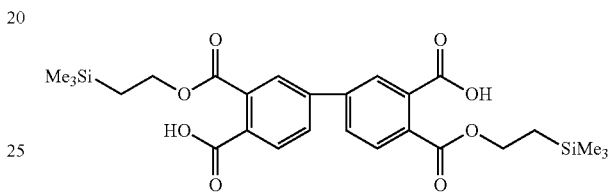

[Synthesis Example 2] Synthesis of Tetracarboxylic Acid Diester Compound (X-2)

In the same manner as in Synthesis Example 1 except for changing 2-(trimethylsilyl)ethanol (Rs-1) to 110.4 g (680 mmol) of 2-(2-trimethylsilylethoxy)ethanol (Rs-2), 200 g of the tetracarboxylic acid diester compound (X-2) having the following structure was obtained.

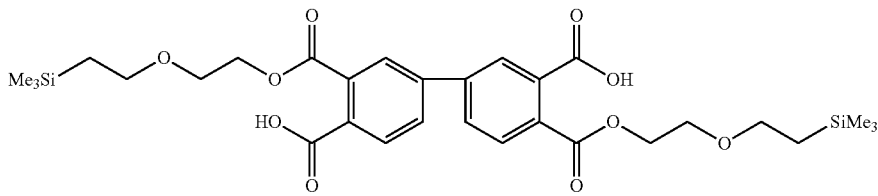 [SMILES: C[Si](C)(C)CCOCCOC(=O)c1ccc(-c2ccc(C(=O)O)c(C(=O)OCCOCC[Si](C)(C)C)c2)cc1C(=O)O]

[Synthesis Example 3] Synthesis of Tetracarboxylic Acid Diester Compound (X-3)

In the same manner as Synthesis Example 1 except for changing 2-(trimethylsilyl)ethanol (Rs-1) to 350 g (680 mmol) of 2-[3-(9-butyl-1,1,3,3,5,5,7,7,9,9-decamethyl-1-pentasiloxanyl)propoxy]-ethanol (Rs-3), 428 g of the tetracarboxylic acid diester compound (X-3) having the following structure was obtained.

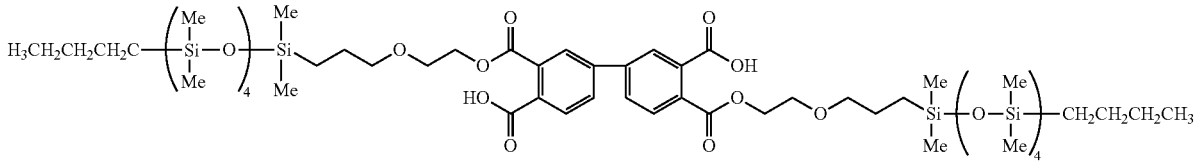

[Synthesis Example 4] Synthesis of Tetracarboxylic Acid Diester Compound (X-4)

In the same manner as Synthesis Example 1 except for changing 2-(trimethylsilyl)ethanol (Rs-1) to 602 g (680 mmol) of X-22-170ASX [available from Shin-Etsu Chemical Co., Ltd.] (Rs-4), 667 g of the tetracarboxylic acid diester compound (X-4) having the following structure was obtained.

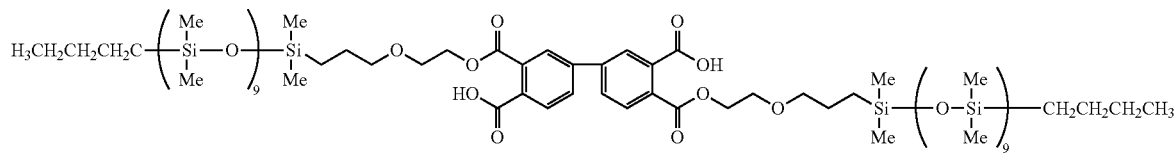

[Synthesis Example 5] Synthesis of Tetracarboxylic Acid Diester Compound (X-5)

In a 3 L of a flask equipped with a stirrer and a thermometer were charged 100 g (322 mmol) of 3,3',4,4'-oxydiphthalic acid dianhydride (s-ODPA), 65.2 g (644 mmol) of trimethylamine, 39.3 g (322 mmol) of N,N-dimethyl-4-aminopyridine and 400 g of γ-butyrolactone, then, 83.8 g (644 mmol) of hydroxyethyl methacrylate (HEMA) was added dropwise to the mixture while stirring at room temperature, and the resulting mixture was stirred under room temperature for 24 hours. Thereafter, under ice-cooling, 370 g of 10% aqueous hydrochloric acid solution was added dropwise to stop the reaction. To the reaction mixture was added 800 g of 4-methyl-2-pentanone, and the organic layer was collected by separation and washed with 600 g of water six times. The solvent of the obtained organic layer was distilled off to obtain 180 g of the tetracarboxylic acid diester compound (X-5) having the following structure.

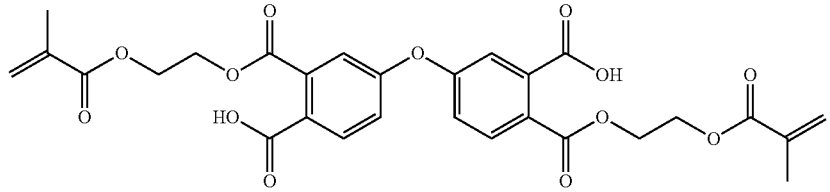 [SMILES: C=C(C)C(=O)OCCOC(=O)c1ccc(Oc2ccc(C(=O)O)c(C(=O)OCCOC(=O)C(=C)C)c2)cc1C(=O)O]

[Synthesis Example 6] Synthesis of Tetracarboxylic Acid Diester Compound (X-6)

In the same manner as Synthesis Example 5 except for changing 3,3',4,4'-oxydiphthalic acid dianhydride (s-ODPA) to 94.8 g (322 mmol) of 3,3',4,4'-bisphthalic acid dianhydride (s-BPDA), 172 g of the tetracarboxylic acid diester compound (X-6) having the following structure was obtained.

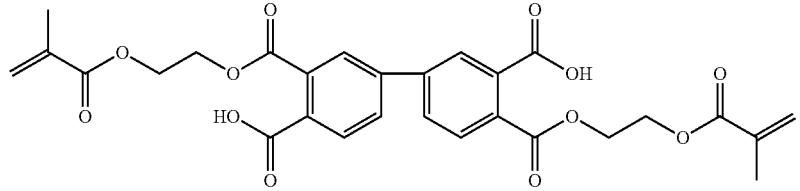 [SMILES: C=C(C)C(=O)OCCOC(=O)c1ccc(-c2ccc(C(=O)O)c(C(=O)OCCOC(=O)C(=C)C)c2)cc1C(=O)O]

[Synthesis Example 7] Synthesis of Polymer of Polyimide Precursor (A-1)

In a 1 L of a flask equipped with a stirrer and a thermometer were charged 26.5 g (50 mmol) of (X-1), 28.5 g (50 mmol) of (X-5) and 278 g of N-methyl-2-pyrrolidone, and the mixture was dissolved by stirring at room temperature. Next, under ice-cooling, 24.4 g (205 mmol) of thionyl chloride was added dropwise to the mixture while maintaining the temperature of the reaction mixture to 10° C. or lower, and after completion of the dropwise addition, the mixture was stirred under ice-cooling for 2 hours. Subsequently, a solution of 19 g (95 mmol) of 4,4'-diaminodiphenyl ether (ODA) and 32.4 g (410 mmol) of pyridine dissolved in 76 g of N-methyl-2-pyrrolidone was added dropwise to the mixture under ice-cooling while maintaining the temperature of the reaction mixture to 10° C. or lower. After completion of the dropwise addition, the temperature of the mixture was returned to room temperature, the reaction mixture was added dropwise into 3 L of water under stirring, the precipitates were collected by filtration and, after optionally washing, dried under reduced pressure at 40° C. for 48 hours to obtain a polymer of a polyimide precursor (A-1). When the molecular weight of the polymer was measured by GPC, it had a weight average molecular weight of 25,000 in terms of the polystyrene.

[Synthesis Example 8] Synthesis of Polymer of Polyimide Precursor (A-2)

In the same manner as Synthesis Example 7 except for changing 26.5 g of (X-1) to 30.9 g (50 mmol) of (X-2), the polymer of a polyimide precursor (A-2) was obtained. When the molecular weight of the polymer was measured by GPC, it had a weight average molecular weight of 27,000 in terms of the polystyrene.

[Synthesis Example 9] Synthesis of Polymer of a Polyimide Precursor (A-3)

In the same manner as Synthesis Example 7 except for changing 26.5 g of (X-1) to 62.5 g (50 mmol) of (X-3), the polymer of a polyimide precursor (A-3) was obtained. When the molecular weight of the polymer was measured by GPC, it had a weight average molecular weight of 30,000 in terms of the polystyrene.

[Synthesis Example 10] Synthesis of Polymer of Polyimide Precursor (A-4)

In the same manner as Synthesis Example 7 except for changing 26.5 g of (X-1) to 97.4 g (50 mmol) of (X-4), the polymer of a polyimide precursor (A-4) was obtained. When the molecular weight of the polymer was measured by GPC, it had a weight average molecular weight of 33,000 in terms of the polystyrene.

[Synthesis Example 11] Synthesis of Polymer of Polyimide Precursor (A-5)

In the same manner as Synthesis Example 9 except for changing 62.5 g of (X-3) to 37.5 g (30 mmol) and 28.5 g of (X-5) to 39.9 g (70 mmol), the polymer of a polyimide precursor (A-5) was obtained. When the molecular weight of the polymer was measured by GPC, it had a weight average molecular weight of 28,000 in terms of the polystyrene.

[Synthesis Example 12] Synthesis of Polymer of Polyimide Precursor (A-6)

In the same manner as Synthesis Example 9 except for changing 62.5 g of (X-3) to 12.5 g (10 mmol) and 28.5 g of (X-5) to 51.3 g (90 mmol), the polymer of a polyimide precursor (A-6) was obtained. When the molecular weight of the polymer was measured by GPC, it had a weight average molecular weight of 26,000 in terms of the polystyrene.

[Synthesis Example 13] Synthesis of Polymer of Polyimide Precursor (A-7)

In the same manner as Synthesis Example 12 except for changing 19 g of ODA to 27.8 g (95 mmol) of 1,3-bis(3-aminophenoxy) 3-benzene (APB), the polymer of a polyimide precursor (A-7) was obtained. When the molecular weight of the polymer was measured by GPC, it had a weight average molecular weight of 28,000 in terms of the polystyrene.

[Synthesis Example 14] Synthesis of Polymer of Polyimide Precursor (A-8)

In a 1 L of a flask equipped with a stirrer and a thermometer were charged 12.5 g (10 mmol) of (X-3), 51.3 g (90 mmol) of (X-5) and 278 g of N-methyl-2-pyrrolidone, and the mixture was dissolved by stirring at room temperature. Next, under ice-cooling, 24.4 g (205 mmol) of thionyl chloride was added dropwise to the mixture while maintaining the temperature of the reaction mixture to 10° C. or lower, and after completion of the dropwise addition, the mixture was stirred under ice-cooling for 2 hours. Subsequently, a solution of 17.1 g (85.5 mmol) of ODA, 2.8 g (9.5 mmol) of APB and 32.4 g (410 mmol) of pyridine dissolved in 76 g of N-methyl-2-pyrrolidone was added dropwise to the mixture under ice-cooling while maintaining the temperature of the reaction mixture to 10° C. or lower. After completion of the dropwise addition, the temperature of the mixture was returned to room temperature, the reaction mixture was added dropwise into 3 L of water under stirring, the precipitates were collected by filtration and, after optionally washing, dried under reduced pressure at 40° C. for 48 hours to obtain a polymer of a polyimide precursor (A-8). When the molecular weight of the polymer was measured by GPC, it had a weight average molecular weight of 28,000 in terms of the polystyrene.

[Comparative Synthesis Example 1] Synthesis of Polymer of Polyimide Precursor (B-1)

In a 1 L of a flask equipped with a stirrer and a thermometer were charged 57.1 g (100 mmol) of (X-5) and 228 g of N-methyl-2-pyrrolidone, and the mixture was dissolved by stirring at room temperature. Next, under ice-cooling, 24.4 g (205 mmol) of thionyl chloride was added dropwise to the mixture while maintaining the temperature of the reaction mixture to 10° C. or lower, and after completion of the dropwise addition, the mixture was stirred under ice-cooling for 2 hours. Subsequently, a solution of 19.0 g (95 mmol) of ODA and 32.4 g (410 mmol) of pyridine dissolved in 76 g of N-methyl-2-pyrrolidone was added dropwise to the mixture under ice-cooling while maintaining the temperature of the reaction mixture to 10° C. or lower. After completion of the dropwise addition, the temperature of the mixture was returned to room temperature, the reaction mixture was added dropwise into 3 L of water under stirring, the precipitates were collected by filtration and, after optionally washing, dried under reduced pressure at 40° C. for 48 hours to obtain a polymer of a polyimide precursor (B-1). When the molecular weight of the polymer was measured by GPC, it had a weight average molecular weight of 18,000 in terms of the polystyrene.

[Comparative Synthesis Example 2] Synthesis of Polymer of Polyimide Precursor (B-2)

In the same manner as Comparative Synthesis Example 1 except for changing 57.1 g of (X-5) to 55.5 g (100 mmol) of (X-6), the polymer of a polyimide precursor (B-2) was obtained. When the molecular weight of the polymer was measured by GPC, it had a weight average molecular weight of 15,000 in terms of the polystyrene.

II. Preparation of Negative Photosensitive Resin Composition (Negative Photosensitive Resin Compositions 1 to 16, Comparative Negative Photosensitive Resin Compositions 1 to 6)

By using the polymers synthesized in the Synthesis Examples 7 to 14 and Comparative Synthesis Examples 1 and 2, resin compositions with 40% by mass in terms of the resin were prepared with the compositions and formulation amounts shown in Tables 1 to 5. Thereafter, the respective compositions were stirred, mixed and dissolved, and then, subjected to microfiltration using a 1.0 μm filter made of Teflon (Registered trademark) to obtain the respective negative photosensitive resin compositions.

TABLE 1

|  | Negative photosensitive resin composition 1 | Negative photosensitive resin composition 2 | Comparative negative photosensitive resin composition 1 | Comparative negative photosensitive resin composition 2 |
|---|---|---|---|---|
| Base resin | A-6 100 parts by weight | A-7 100 parts by weight | B-1 100 parts by weight | B-2 100 parts by weight |
| Photoradical initiator | Photoradical initiator 1 2 parts by weight | Photoradical initiator 1 2 parts by weight | Photoradical initiator 1 2 parts by weight | Photoradical initiator 1 2 parts by weight |
| Crosslinking agent | — | — | — | — |
| Solvent | NMP 150 parts by weight | NMP 150 parts by weight | NMP 150 parts by weight | NMP 150 parts by weight |

The negative photosensitive resin compositions 1 and 2 shown in Table 1 relates to the negative photosensitive resin composition of the first embodiment of the present invention. Comparative negative photosensitive resin compositions 1 and 2 are materials in which, in the negative photosensitive resin composition of the first embodiment of the present invention, the polymers of a polyimide precursor synthesized in Comparative Synthesis Examples 1 and 2 were used as the base resin in place of the polymer of a polyimide precursor of the present invention.

TABLE 2

|  | Negative photosensitive resin composition 3 | Negative photosensitive resin composition 4 | Negative photosensitive resin composition 5 | Negative photosensitive resin composition 6 | Negative photosensitive resin composition 7 |
|---|---|---|---|---|---|
| Base resin | A-1 100 parts by weight | A-2 100 parts by weight | A-3 100 parts by weight | A-4 100 parts by weight | A-5 100 parts by weight |
| Photoradical initiator | Photoradical initiator 1 2 parts by weight | Photoradical initiator 1 2 parts by weight | Photoradical initiator 1 2 parts by weight | Photoradical initiator 1 2 parts by weight | Photoradical initiator 1 2 parts by weight |
| Crosslinking agent | CL-1 15 parts by weight | CL-1 15 parts by weight | CL-1 15 parts by weight | CL-1 15 parts by weight | CL-1 15 parts by weight |
| Solvent | NMP 150 parts by weight | NMP 150 parts by weight | NMP 150 parts by weight | NMP 150 parts by weight | NMP 150 parts by weight |

TABLE 3

|  | Negative photosensitive resin composition 8 | Negative photosensitive resin composition 9 | Negative photosensitive resin composition 10 | Comparative negative photosensitive resin composition 3 | Comparative negative photosensitive resin composition 4 |
|---|---|---|---|---|---|
| Base resin | A-6 100 parts by weight | A-7 100 parts by weight | A-8 100 parts by weight | B-1 100 parts by weight | B-2 100 parts by weight |
| Photoradical initiator | Photoradical initiator 1 2 parts by weight | Photoradical initiator 1 2 parts by weight | Photoradical initiator 1 2 parts by weight | Photoradical initiator 1 2 parts by weight | Photoradical initiator 1 2 parts by weight |
| Crosslinking agent | CL-1 15 parts by weight | CL-1 15 parts by weight | CL-1 15 parts by weight | CL-1 15 parts by weight | CL-1 15 parts by weight |
| Solvent | NMP 150 parts by weight | NMP 150 parts by weight | NMP 150 parts by weight | NMP 150 parts by weight | NMP 150 parts by weight |

The negative photosensitive resin compositions 3 to 10 shown in Tables 2 and 3 relate to the negative photosensitive resin composition of the second embodiment of the present invention. Comparative negative photosensitive resin compositions 3 and 4 shown in Table 3 are materials in which, in the negative photosensitive resin composition of the second embodiment of the present invention, the polymers of a polyimide precursor synthesized in Comparative Synthesis Examples 1 and 2 were used as the base resin in place of the polymer of a polyimide precursor of the present invention.

TABLE 4

|  | Negative photosensitive resin composition 11 | Negative photosensitive resin composition 12 | Negative photosensitive resin composition 13 | Negative photosensitive resin composition 14 |
|---|---|---|---|---|
| Base resin | A-1 100 parts by weight | A-2 100 parts by weight | A-3 100 parts by weight | A-4 100 parts by weight |
| Photoacid generator | Photoacid generator 1 2 parts by weight | Photoacid generator 1 2 parts by weight | Photoacid generator 1 2 parts by weight | Photoacid generator 1 2 parts by weight |
| Crosslinking agent | CL-2 15 parts by weight | CL-2 15 parts by weight | CL-2 15 parts by weight | CL-2 15 parts by weight |
| Crosslinking agent | CL-3 15 parts by weight | CL-3 15 parts by weight | CL-3 15 parts by weight | CL-3 15 parts by weight |
| Solvent | NMP 150 parts by weight | NMP 150 parts by weight | NMP 150 parts by weight | NMP 150 parts by weight |

TABLE 5

|  | Negative photosensitive resin composition 15 | Negative photosensitive resin composition 16 | Comparative negative photosensitive resin composition 5 | Comparative negative photosensitive resin composition 6 |
|---|---|---|---|---|
| Base resin | A-7 100 parts by weight | A-8 100 parts by weight | B-1 100 parts by weight | B-2 100 parts by weight |
| Photoacid generator | Photoacid generator 1 2 parts by weight | Photoacid generator 1 2 parts by weight | Photoacid generator 1 2 parts by weight | Photoacid generator 1 2 parts by weight |
| Crosslinking agent | CL-2 15 parts by weight | CL-2 15 parts by weight | CL-2 15 parts by weight | CL-2 15 parts by weight |
| Crosslinking agent | CL-3 15 parts by weight | CL-3 15 parts by weight | CL-3 15 parts by weight | CL-3 15 parts by weight |
| Solvent | NMP 150 parts by weight | NMP 150 parts by weight | NMP 150 parts by weight | NMP 150 parts by weight |

The negative photosensitive resin compositions 11 to 16 shown in Tables 4 and 5 relate to the negative photosensitive resin composition of the third embodiment of the present invention. Comparative negative photosensitive resin compositions 5 and 6 shown in Table 5 are materials in which, in the negative photosensitive resin composition of the third embodiment of the present invention, the polymers of a polyimide precursor synthesized in Comparative Synthesis Examples 1 and 2 were used as the base resin in place of the polymer of a polyimide precursor of the present invention.

In Tables 1 to 5, details of the photoradical initiator (photoradical initiator 1), the photoacid generator (photoacid generator 1), the crosslinking agents (CL-1) to (CL-3) are as follows.

Photoradical initiator (Photoradical initiator 1): NP-1919 available from ADEKA Corporation Photoacid Generator (Photoacid Generator 1)

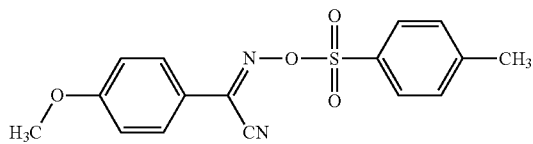

Crosslinking Agent (CL-1): Ethylene Glycol Diacrylate
Crosslinking Agent (CL-2)

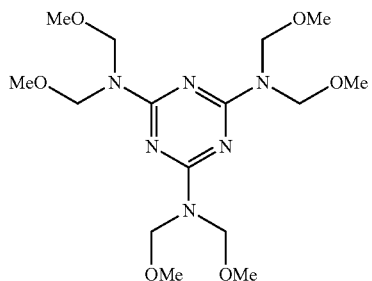 [SMILES: COCN(COC)c1nc(N(COC)COC)nc(N(COC)COC)n1]

Crosslinking Agent (CL-3),

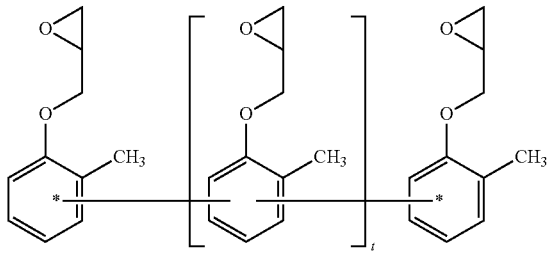

wherein, "t" is $2 \leq t \leq 3$.

III. Patterning

The negative photosensitive resin compositions 1 to 16 and Comparative negative photosensitive resin compositions 1 to 6 were dispensed on a silicon substrate with 5 mL, and then, the substrate was rotated, that is, by the spin coating method, so as to have a film thickness of 10 μm after heating for post-curing applied after patterning. That is, it was examined beforehand that the film thickness decreased after the post-curing, and the rotational speed at the time of coating was adjusted so that the finished film thickness after the post-curing would be 10 μm.

Next, prebaking was applied on a hot plate at 100° C. for 2 minutes. Then, i-line exposure and patterning were carried out using an i-line stepper NSR-2205i11 manufactured by Nikon Corporation. In the patterning, a mask for a negative type pattern was suitably used in accordance with the negative photosensitive resin composition used. The mask had a pattern capable of forming 20 μm holes arranged with a 1:1 ratio lengthwise and breadthwise, and permitted to form a hole pattern of 50 μm to 20 μm holes with 10-μm pitch, 20 μm to 10 μm holes with 5-μm pitch, and 10 μm to 1 μm holes with 1-μm pitch.

With regard to the heating after exposure (post-exposure bake), it was not carried out in any of the examples as shown in the following Tables 6 to 8.

In the development, cyclopentanone was used as the developer in Examples 1 to 16. On the other hand, NMP was used as the developer in Comparative negative photosensitive resin compositions 1 to 6 prepared as Comparative examples. Development by an organic solvent was carried out by a paddle development of each organic solvent for 1 minutes with a number of times shown in Tables 6 to 8, and rinsing was carried out with isopropyl alcohol.

Then, the obtained pattern on the substrate was subjected to post-curing using an oven at 250° C. for 2 hours while purging with nitrogen.

Next, each substrate was cut out so that the profile of the obtained hole pattern can be observed, and a profile of the hole pattern was observed by using a scanning type electron microscope (SEM). An aperture diameter of the smallest opening hole at a film thickness of 10 μm after post-curing was obtained, and the pattern profile was evaluated.

Together with these results, the sensitivities at which the minimum pattern could be formed are shown in Tables 6 to 8.

The hole pattern profile was evaluated by the following standard, and the evaluation results were shown in the following Tables 6 to 8.

Good: that in which rectangular or forward taper shape hole (the shape in which the size of the hole upper part is larger than the size of the bottom part) was observed Not good: that in which reverse taper shape (the shape in which the size of the hole upper part is smaller than the size of the bottom part), overhang shape (the shape in which the hole upper part protrudes), or residue at the bottom part of the hole was observed First, by using the negative photosensitive resin compositions 1 and 2 (the negative photosensitive resin composition of the first embodiment of the present invention), and Comparative negative photosensitive resin compositions 1 and 2, development by an organic solvent patterning was carried out. The results are shown in Table 6.

TABLE 6

|  | Negative photosensitive composition | Pattern | Bake after exposure | Developer | Development condition | Hole shape | Minimum hole diameter (um) | Sensitivity (mJ/cm$^2$) |
| --- | --- | --- | --- | --- | --- | --- | --- | --- |
| Example 1 | Negative photosensitive composition 1 | Negative | None | Organic solvent developer (cyclopentanone) | Paddle 60 sec. twice | Good | 8 | 320 |
| Example 2 | Negative photosensitive composition 2 | Negative | None | Organic solvent developer (cyclopentanone) | Paddle 60 sec. twice | Good | 8 | 320 |
| Comparative example 1 | Comparative negative photosensitive composition 1 | Negative | None | Organic solvent developer (NMP) | Paddle 60 sec. twice | Not good | 20 | 400 |
| Comparative example 2 | Comparative negative photosensitive composition 2 | Negative | None | Organic solvent developer (NMP) | Paddle 60 sec. twice | Not good | 20 | 420 |

Next, by using the negative photosensitive resin compositions 3 to 10 (the negative photosensitive resin compositions of the second embodiment of the present invention), and Comparative negative photosensitive resin compositions 3 and 4, pattern-forming is carried out by development by an organic solvent. The results were shown in Table 7.

TABLE 7

|  | Negative photosensitive composition | Pattern | Bake after exposure | Developer | Development condition | Hole shape | Minimum hole diameter (um) | Sensitivity (mJ/cm$^2$) |
| --- | --- | --- | --- | --- | --- | --- | --- | --- |
| Example 3 | Negative photosensitive composition 3 | Negative | None | Organic solvent developer (cyclopentanone) | Paddle 60 sec. once | Good | 6 | 340 |
| Example 4 | Negative photosensitive composition 4 | Negative | None | Organic solvent developer (cyclopentanone) | Paddle 60 sec. once | Good | 7 | 340 |
| Example 5 | Negative photosensitive composition 5 | Negative | None | Organic solvent developer (cyclopentanone) | Paddle 60 sec. once | Good | 6 | 330 |
| Example 6 | Negative photosensitive composition 6 | Negative | None | Organic solvent developer (cyclopentanone) | Paddle 60 sec. once | Good | 7 | 330 |

TABLE 7-continued

| | Negative photosensitive composition | Pattern | Bake after exposure | Developer | Development condition | Hole shape | Minimum hole diameter (um) | Sensitivity (mJ/cm²) |
|---|---|---|---|---|---|---|---|---|
| Example 7 | Negative photosensitive composition 7 | Negative | None | Organic solvent developer (cyclopentanone) | Paddle 60 sec. once | Good | 8 | 320 |
| Example 8 | Negative photosensitive composition 8 | Negative | None | Organic solvent developer (cyclopentanone) | Paddle 60 sec. once | Good | 8 | 310 |
| Example 9 | Negative photosensitive composition 9 | Negative | None | Organic solvent developer (cyclopentanone) | Paddle 60 sec. once | Good | 8 | 310 |
| Example 10 | Negative photosensitive composition 10 | Negative | None | Organic solvent developer (cyclopentanone) | Paddle 60 sec. once | Good | 8 | 310 |
| Comparative example 3 | Comparative negative photosensitive composition 3 | Negative | None | Organic solvent developer (NMP) | Paddle 60 sec. twice | Not good | 20 | 360 |
| Comparative example 4 | Comparative negative photosensitive composition 4 | Negative | None | Organic solvent developer (NMP) | Paddle 60 sec. twice | Not good | 20 | 380 |

Further, by using the negative photosensitive resin compositions 11 to 16 (the negative photosensitive resin compositions of the third embodiment of the present invention), and Comparative negative photosensitive resin compositions 5 and 6, pattern-forming is carried out by development by an organic solvent. The results were shown in Table 8.

TABLE 8

| | Negative photosensitive composition | Pattern | Bake after exposure | Developer | Development condition | Hole shape | Minimum hole diameter (um) | Sensitivity (mJ/cm²) |
|---|---|---|---|---|---|---|---|---|
| Example 11 | Negative photosensitive composition 11 | Negative | None | Organic solvent developer cyclopentanone | Paddle 60 sec. once | Good | 7 | 380 |
| Example 12 | Negative photosensitive composition 12 | Negative | None | Organic solvent developer cyclopentanone | Paddle 60 sec. once | Good | 7 | 380 |
| Example 13 | Negative photosensitive composition 13 | Negative | None | Organic solvent developer cyclopentanone | Paddle 60 sec. once | Good | 6 | 390 |
| Example 14 | Negative photosensitive composition 14 | Negative | None | Organic solvent developer cyclopentanone | Paddle 60 sec. once | Good | 7 | 400 |
| Example 15 | Negative photosensitive composition 15 | Negative | None | Organic solvent developer cyclopentanone | Paddle 60 sec. once | Good | 8 | 380 |
| Example 16 | Negative photosensitive composition 16 | Negative | None | Organic solvent developer cyclopentanone | Paddle 60 sec. once | Good | 8 | 380 |
| Comparative example 5 | Comparative negative photosensitive composition 5 | Negative | None | Organic solvent developer NMP | Paddle 60 sec. twice | Not good | 20 | 480 |
| Comparative example 6 | Comparative negative photosensitive composition 6 | Negative | None | Organic solvent developer NMP | Paddle 60 sec. twice | Not good | 20 | 520 |

As shown in Tables 6 to 8, the negative photosensitive resin compositions of the present invention show good pattern profile in the development by an organic solvent, and the minimum hole diameter thereof show smaller values as compared with the finished film thickness of 10 μm, so that it can be understood that the aspect ratio of 1 or more can be accomplished.

On the other hand, in the patterning of Comparative negative photosensitive resin compositions 1 to 6 using the polymers of a polyimide precursor which do not contain the group containing at least one silicon atom at the terminal of the substituent shown as Comparative examples, in the development by an organic solvent using cyclopentanone, the base resins themselves in Comparative negative photosensitive resin compositions are difficulty soluble or insoluble in cyclopentanone, so that the patterning using NMP must be carried out.

In the patterning of Comparative negative photosensitive resin compositions 1 to 6 shown as Comparative examples in the Tables 6 to 8, when NMP was used, pattern could be obtained. However, the pattern dimension was large so that the aspect ratio of 1 or more cannot be accomplished. In addition, in many of the patterns, overhanging profile was observed, and the pattern profile was poor. Observation of the overhanging profile is considered to be due to swelling of the pattern during the development.

It must be stated here that the present invention is not restricted to the embodiments shown by Examples. The embodiments shown by Examples are merely examples so that any embodiments composed of substantially the same technical concept as disclosed in the claims of the present invention and expressing a similar effect are included in the technical scope of the present invention.

The invention claimed is:

1. A tetracarboxylic acid diester compound represented by the following general formula (1),

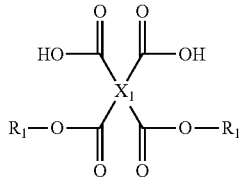

(1)

wherein, $X_1$ represents a tetravalent organic group, and $R_1$ represents a group represented by the following general formula (4),

(4)

wherein, the dotted line represents a bonding, Rs represents a group containing at least one silicon atom, $Y_2$ represents a linear or branched alkylene group having 1 to 6 carbon atoms, "n2" represents an integer of 1 to 6 and "n3" represents an integer of 1 to 6.

2. The tetracarboxylic acid diester compound according to claim 1, wherein $R_1$ in the general formula (1) is a group represented by the following general formula (5),

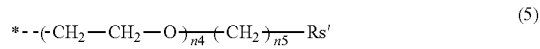

(5)

wherein, the dotted line represents a bonding, "n4" represents an integer of 1 to 6, "n5" represents an integer of 1 to 6 and Rs' represents a group represented by the following general formula (6),

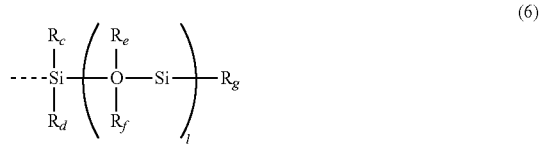

(6)

wherein, $R_c$ to $R_g$ each may be the same or different from each other and represent a monovalent hydrocarbon group having 1 to 8 carbon atoms, and "l" represents an integer of 1 to 100.

* * * * *